United States Patent [19]

Nagasaki et al.

[11] Patent Number: 5,506,912
[45] Date of Patent: Apr. 9, 1996

[54] IMAGING DEVICE CAPABLE OF TRACKING AN OBJECT

[75] Inventors: Tatsuo Nagasaki, Yokohama; Yasuhiro Komiya, Hachioji, both of Japan

[73] Assignee: Olympus Optical Co., Ltd., Tokyo, Japan

[21] Appl. No.: 336,793

[22] Filed: Nov. 9, 1994

Related U.S. Application Data

[63] Continuation of Ser. No. 66,631, May 24, 1993, abandoned, which is a continuation of Ser. No. 853,357, Mar. 16, 1992, abandoned, which is a continuation of Ser. No. 644,130, Jan. 18, 1991, abandoned.

[30] Foreign Application Priority Data

Jan. 26, 1990  [JP]  Japan ........................................ 2-15048

[51] Int. Cl.$^6$ .................................................. H04N 7/18
[52] U.S. Cl. ........................... 382/103; 382/128; 382/255; 348/65; 600/103
[58] Field of Search ...................... 382/6, 17, 48; 128/4, 6; 348/65, 169, 351

[56] References Cited

U.S. PATENT DOCUMENTS

| | | | |
|---|---|---|---|
| 3,736,376 | 5/1973 | Kato, Jr. ................................ | 358/126 |
| 4,364,089 | 12/1982 | Woolfson ............................... | 358/125 |
| 4,563,705 | 1/1986 | Oinoue et al. ......................... | 358/227 |
| 4,788,596 | 11/1988 | Kawakami et al. .................... | 358/222 |
| 4,864,409 | 9/1989 | Platte et al. ........................... | 358/222 |
| 4,928,174 | 5/1990 | Smith .................................... | 358/108 |
| 5,012,270 | 4/1991 | Sekine et al. .......................... | 358/222 |

FOREIGN PATENT DOCUMENTS

| | | |
|---|---|---|
| 3630385A1 | 3/1987 | Germany . |
| 3243920C2 | 6/1987 | Germany . |
| 3733593A1 | 4/1989 | Germany . |
| 3907664A1 | 10/1989 | Germany . |
| 2220319 | 1/1990 | United Kingdom . |
| WO90/00334 | 1/1990 | WIPO . |

OTHER PUBLICATIONS

"Intelligent Digital Image Stabilizer", by Kenya Uomori et al, pp. 177–180.
"Video Movement Stabilizer", by Kouei Kawamura et al; pp. 377–378.

*Primary Examiner*—Leo Boudreau
*Assistant Examiner*—Chris Kelley
*Attorney, Agent, or Firm*—Frishauf, Holtz, Goodman, Langer & Chick

[57] ABSTRACT

An imaging device having a signal-processing section, an imaging section, and X- and Y-direction angle wire drivers. The imaging section sequentially form images of an object. The signal-processing section obtains X- and Y-direction displacements of the imaging section with respect to an object, from the positional relationship between the images formed by the imaging section. The angle wire drivers drive X- and Y-direction angle wires in accordance with the X- and Y-direction displacements obtained by the signal-processing section, thus moving the imaging section such that the imaging section tracks the object.

45 Claims, 13 Drawing Sheets

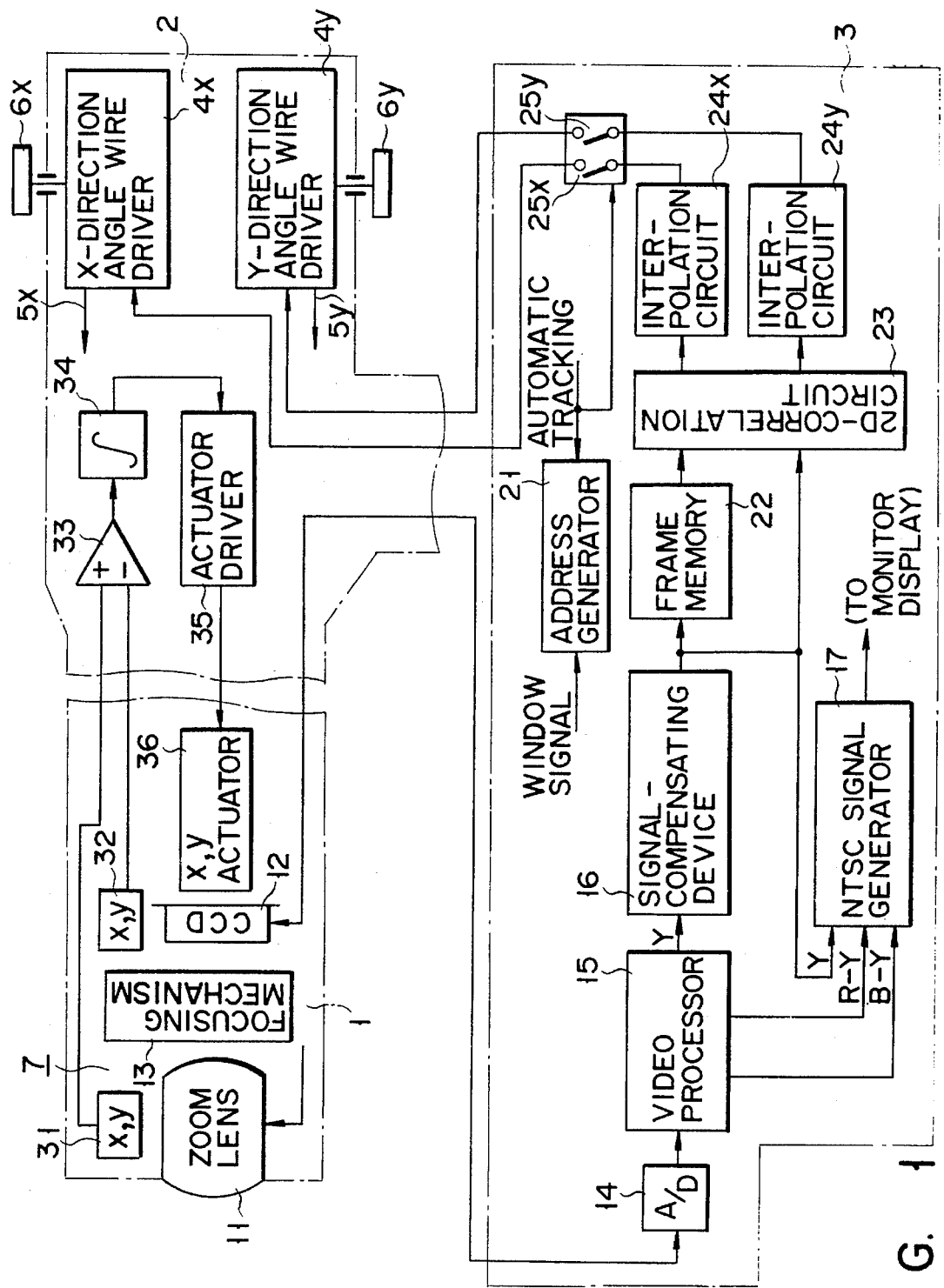
F I G. 1

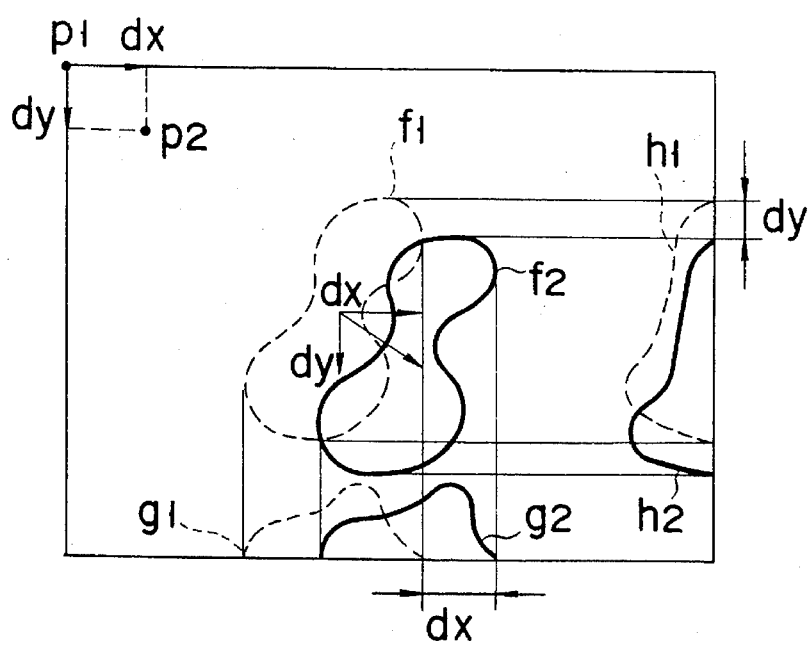
F I G. 2
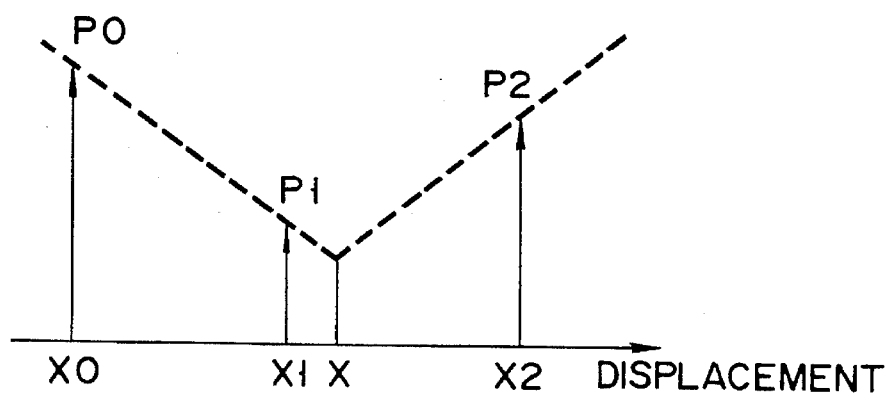
F I G. 3

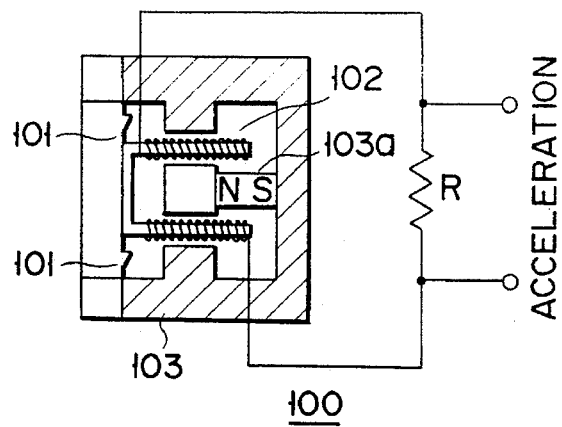
F I G. 4
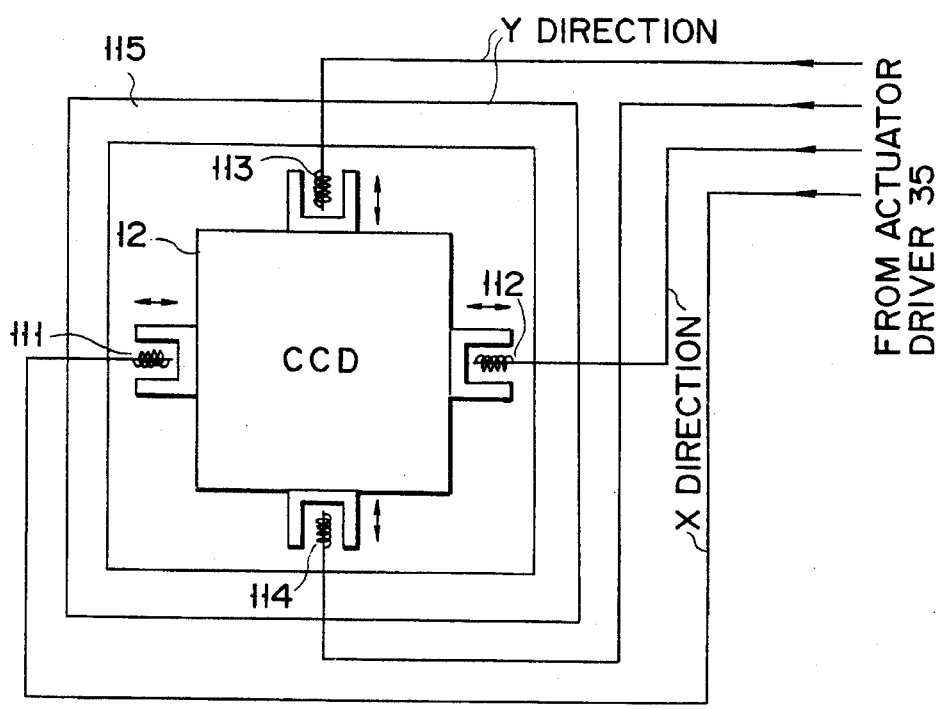
F I G. 5

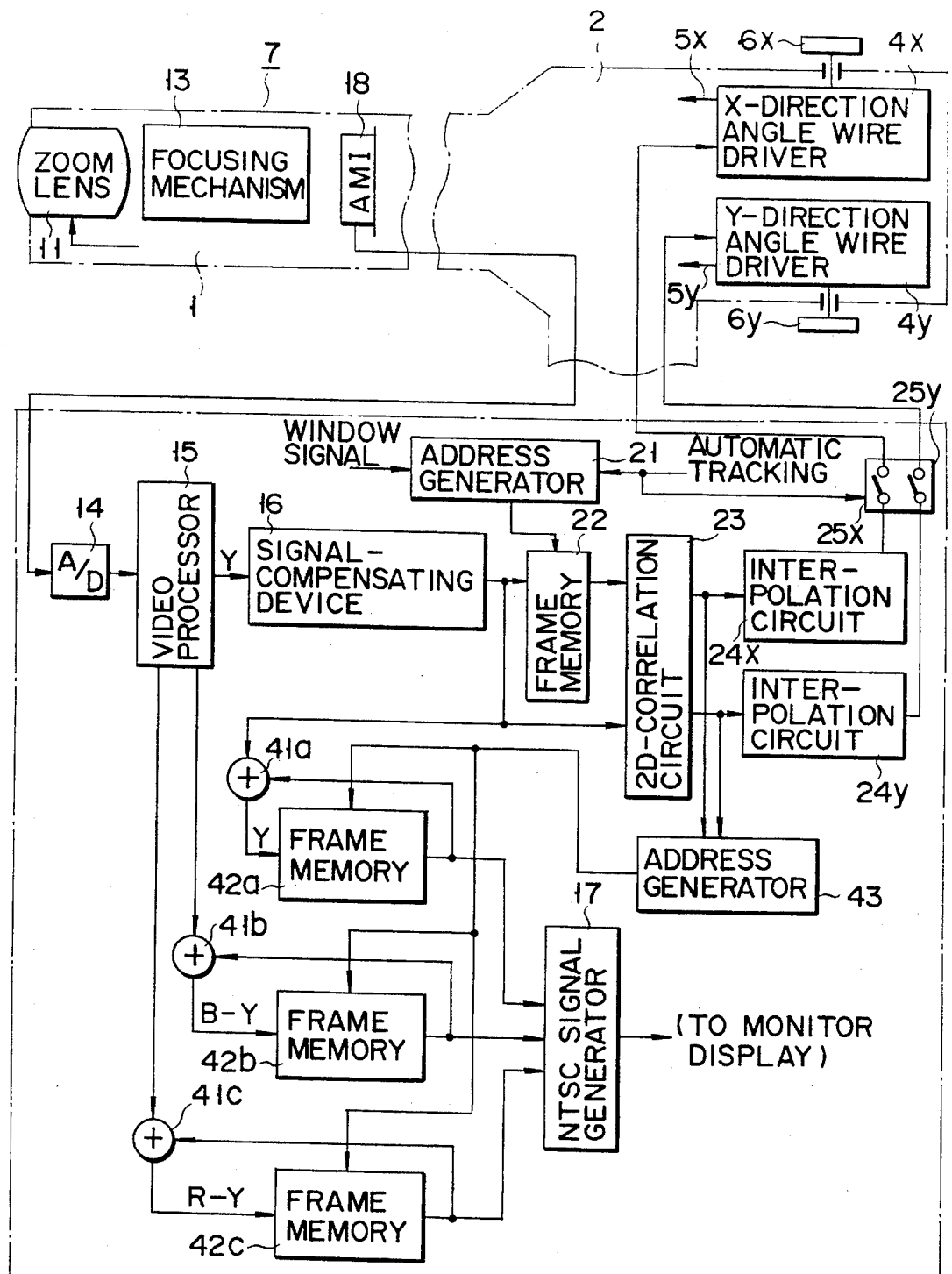
F I G. 7

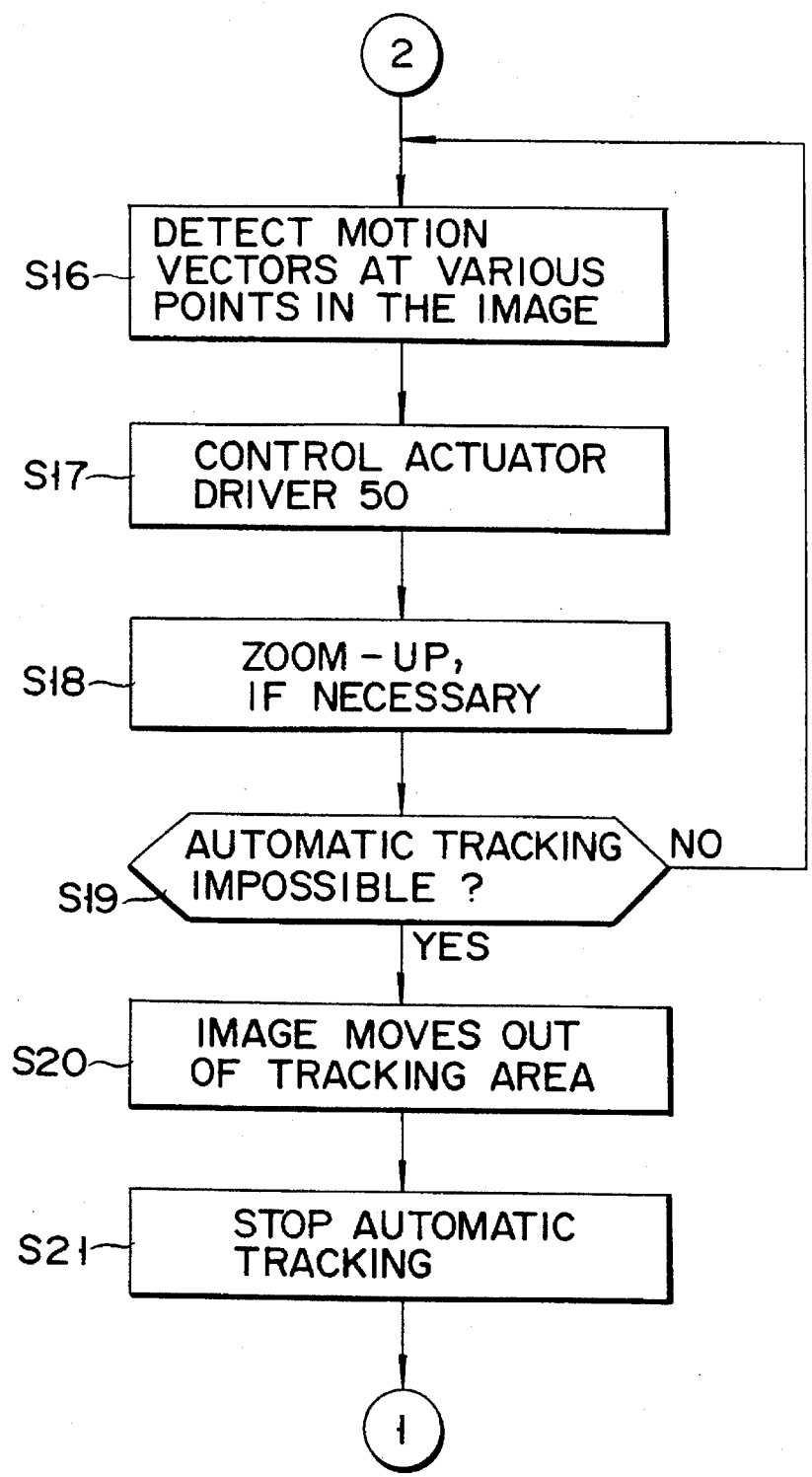
F I G. 12B

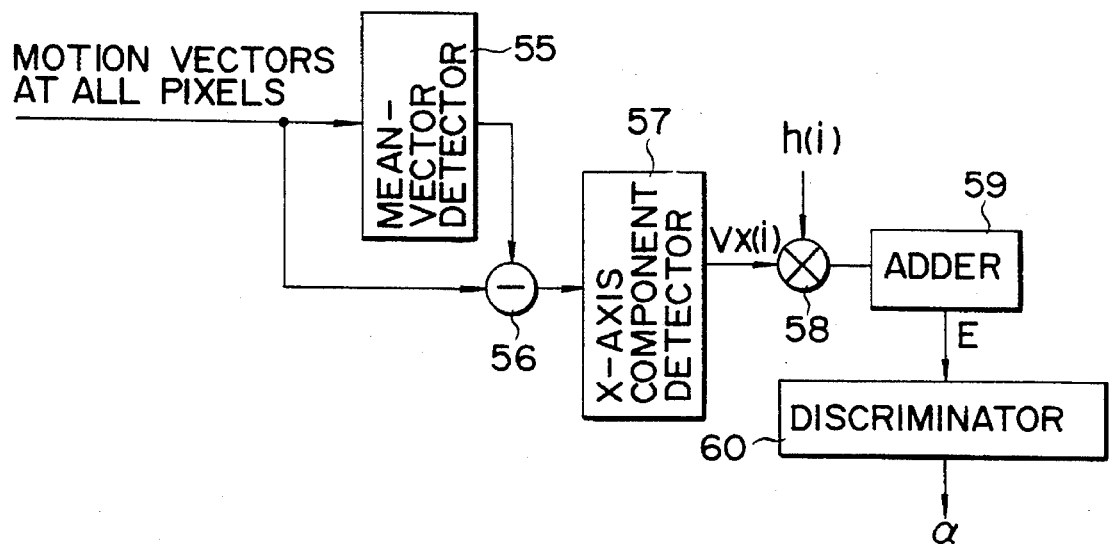
F I G. 16
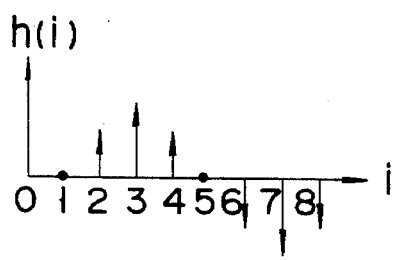
F I G. 17

IMAGING DEVICE CAPABLE OF TRACKING AN OBJECT

This application is a Continuation, of application Ser. No. 08/066,631, filed May 24, 1993, (now abandoned) which is a continuation of Ser. No. 07/853,357, filed Mar. 16, 1992 (now abandoned), which is a continuation of Ser. No. 07/644,130 filed Jan. 18, 1991 (now abandoned)

BACKGROUND OF THE INVENTION

1. Field of the Invention

This invention relates to an imaging device to be incorporated in an endoscope or a microscope and, in particular to an imaging device which comprises an imaging section and means for compensating any displacement between the imaging section and an object of photography.

2. Description of the Related Art

In recent years, solid-state image sensors have been into made smaller and smaller. The miniaturized image sensors are built in imaging devices, which in turn are incorporated in endoscopes and microscopes. These devices convert the images of objects into electric signals. The electric signals are supplied to television receivers or the like, whereby the images of the objects are monitored. Further, the electronic still images the imaging devices have formed are recorded on recording media such as floppy disks or memory cards.

The imaging device incorporated in an endoscope or a microscope is operated in the following way, in order to record the image of an object. First, the operator places the device near the object, and turns on the power switch of the device, thereby to photograph the object. Then, while viewing the image formed by the device and displayed on a monitor screen, he or she moves the device until the imaging section picks up the image of the object. Further, he or she operates the device, thereby "freezing" the position of the imaging section. More specifically, the operator manipulates the positioning mechanism built in the device, thus moving the imaging section to a position which is desirable with respect to the object. After freezing the position of the imaging section, the operator pushes the record button of the device, whereby the image of the object, formed by the imaging section set at the desirable position, is recorded on a recording medium.

In the case where the imaging device is used in an endoscope, its imaging section is located within the distal end portion of the insertion section of the endoscope. The endoscope has a positioning mechanism which comprises an angle wire or the like and which is designed to move the distal end of the insertion section in a plane perpendicular to the optical axis of the imaging section and to set the distal end at a position desired with respect to an object existing in a body cavity. In some cases, the positioning mechanism is operated such that the imaging section gradually moves toward the object until it reaches the desired position.

As the imaging section is moved little by little, toward the desirable position of the object, it unavoidably vibrates. To make matters worse, the object is not always stationary, possibly moving, in which case the imaging section vibrates relative to the object. The image reconstructed from the electric signals supplied from the imaging section inevitably oscillates on the monitor screen so swiftly that the operator can hardly recognize the object correctly. Consequently, it is difficult for the operator to track the object by moving the distal end portion of the insertion section. If the operator pushes the record button while the image on the monitor screen is oscillating, the image recorded will be too unclear.

SUMMARY OF THE INVENTION

The object of the present invention is to provide an imaging device which comprises an imaging section and means for compensating any displacement between the imaging section and an object, and which can therefore form a very clear image of the object and is thus of great practical value.

According to the invention, there is provided an imaging device which comprises:

an imaging section for electronically imaging an object;

displacement-calculating means for calculating the displacement between the object and the imaging section, from the positional relationship among the images of the object which are sequentially formed by the imaging section; and object-tracking means for moving the imaging section for a distance equal to the displacement calculated by the displacement-calculating means, thereby to cause the imaging section to track the object.

In the imaging device, the positioning mechanism of the imaging section, such as an angle wire mechanism, is automatically operated in accordance with the displacement between the object and the imaging section, which said displacement-calculating means has calculated. The imaging section thereby follows the object, successfully eliminating the displacement between the object and the imaging section. As a result, the image formed by the imaging section does not move on a monitor screen, and is therefore sufficiently clear.

The imaging section comprises displacement sensors, an optical lens system, and a solid-state image sensor. Each displacement sensor is, for example, an acceleration sensor and detects the displacement between the object and the imaging section. The positional relationship between the lens system and the object and also the positional relationship between the image sensor and the object are changed in accordance with the displacement, thereby compensating for the displacement between the object and the imaging section.

Since the imaging section is moved to track the object, thereby correcting the positional relation between the lens system and the object and that between the image sensor and the object, the displacement between the object and the imaging section can be eliminated at high speed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 schematically illustrates an endoscope having an imaging device according to a first embodiment of the present invention;

FIG. 2 is a diagram explaining how to detect the displacement between two images of an object formed sequentially by the imaging section incorporated in the imaging device;

FIG. 3 is a graph explaining how to interpolate the displacement between the images formed by the imaging section;

FIG. 4 is a sectional view showing the acceleration sensor unit used in the imaging section;

FIG. 5 is a schematic representation of an XY actuator incorporated in the imaging section;

FIG. 7 schematically illustrates an endoscope having an imaging device according to a second embodiment of the present invention;

FIGS. 12A and 12B form a flow chart explaining the operation of the imaging device illustrated in FIG. 9;

FIG. 16 is a diagram explaining the method of determining the ratio α of image enlargement/reduction;

FIG. 17 is a graph explaining the function h(i) used to determine whether an image has been enlarged or reduced.

DETAILED DESCRIPTION OF THE PREFERRED EMBODIMENTS

Figure 6:
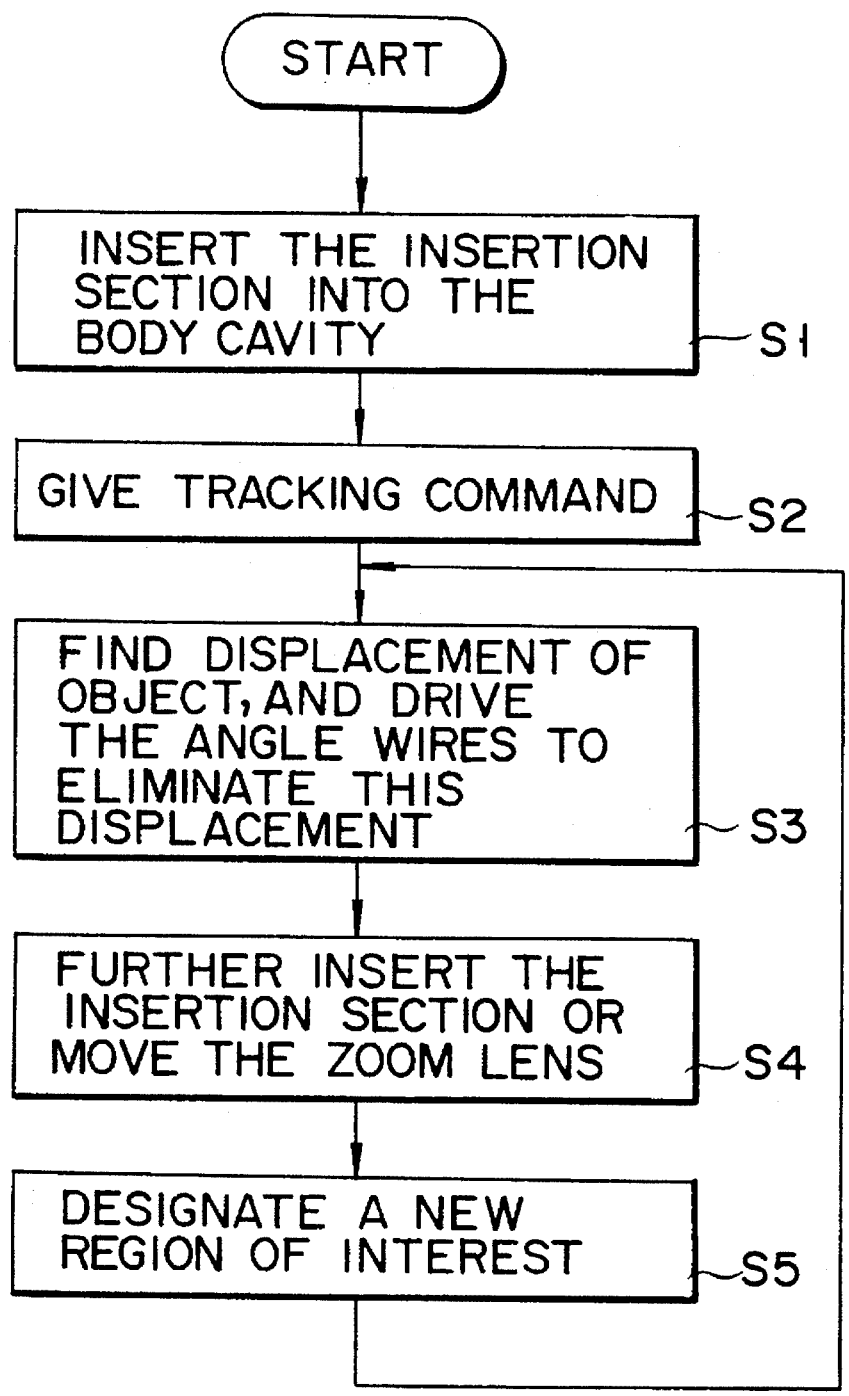
FIG. 6 is a flow chart explaining the operation of the imaging device illustrated in FIG. 1.

FIG. 1 shows an endoscope having an imaging device according to a first embodiment of the present invention. The endoscope comprises an insertion section 1, an operation section 2, and a signal-processing section 3. The operation section 2 contains a positioning mechanism which has an X-direction angle wire driver 4x, a Y-direction angle wire driver 4y, two angle wires 5x and 5y, and two knobs 6x and 6y. The wires 5x and 5y are connected, at distal end, to the distal end of the insertion section 1, respectively. They are connected, at proximal end, to the wire drivers 4x and 4y, respectively. The wire drivers 4x and 4y are connected to the knobs 6x and 6y, respectively. When an operator turns the knobs 6x and 6y in one direction or the other, the drivers 4x and 4y pull or slacken the angle wires 5x and 5y, whereby the distal end of the insertion section 1 is moved in the X direction and Y direction in a plane perpendicular to the axis of the insertion section 1.

Most endoscopes used at present which has a bundle of optical fibers which extends through the insertion section, from the operation section to the distal end of the insertion section. Therefore, the operator can see the interior of a body cavity as long as the insertion section is inserted in the cavity. With the endoscope shown in FIG. 1, the operator turns the knobs 6x and 6y, while seeing the interior of the cavity, whereby the angle wires 5x and 5y are pulled or slackened, moving the distal end of the section 1 in the X and Y directions until the distal end is positioned near an object within the body cavity.

The endoscope has no optical fiber, and comprises an imaging section 7 located within the distal end portion of the insertion section 1. The section 7 is designed to generate image signals representing an image of the object. The image signals are supplied to the signal-processing section 3. The section 3 converts these signals into so-called TV (television) signals. The TV signals are supplied from the section 3 to an image monitor (e.g., a TV receiver), which displays the image of the object on its display screen. Hence, the object within the body cavity can be monitored.

The imaging section 7 comprises a optical lens system and a solid-state image sensor. The lens system forms an image of an object on the imaging surface of the image sensor. The image sensor converts the image into image signals. More specifically, the lens system comprises a zoom lens 11 and a relay lens (not shown), and the solid-state image sensor is a CCD (Charge-Coupled Device) 12. A focusing mechanism 13 is located between the zoom lens 11 and the CCD 12, and moves the relay lens at high speed, back and forth in the optical path between the lens 11 and the CCD 12, thereby changing the focal depth of the optical lens system.

As the knobs 6x and 6y are turned, the X-direction angle wire driver 4x and the Y-direction angle wire driver 4y operate, moving the distal end of the insertion section 1 within the body cavity, in a plane which is perpendicular to the optical axis of the section 1, thereby eliminating the displacement between the object and the imaging section 7.

The image signals, which have been generated by the CCD 12 and representing the image of the object, are supplied to the signal-processing section 3 through a signal line extending in the insertion section 1. The section 3 comprises an A/D converter 14, a video processor 15, a signal-compensating device 16, an NTSC signal generator 17, an address generator 21, a frame memory 22, a two-dimensional correlation circuit 23, two interpolation circuits 24x and 24y, and two switches 25x and 25y.

The A/D converter 14 converts the image signals into digital signals. The digital signals are supplied to the video processor 15. The video processor 15 processes the digital image signals, decomposing each signal into one luminance signal Y and two color-difference signals (R-Y) and (B-Y). The luminance signal Y is supplied to the signal-compensating device 16, which adds a required component to the luminance signal Y. (This device 16 is of the type disclosed in U.S. patent Ser. No. 312,021 the applicants hereof filed on Feb. 16, 1989.) The luminance signal Y, thus compensated is supplied to the NTSC signal generator 17, along with the color-difference signals (R-Y) and (B-Y). The NTSC signal generator 17 produces an NTSC-standard TV signal from the luminance signal Y and the two color-difference signals (R-Y) and (B-Y). The TV signal is supplied to the image monitor (i.e., the TV receiver, not shown). Other TV signals which the generator 17 has sequentially produced are supplied to the monitor. Hence, the monitor displays the image of the object on its display screen.

The luminance signal Y, which has been generated by the video processor 15 from an image signal output from the CCD 12 and then compensated by the signal-compensating device 16, is utilized to determine the displacement of the imaging section 7 with respect to the object within the body cavity. In accordance with the displacement, thus determined, the wire drivers 4x and 4y are negative feedback-controlled, thereby to move the distal end of the insertion section 1 in the plane perpendicular to the optical axis of the section 7. As a result of this, the distal end of the section tracks the object, eliminating the displacement between the object and the imaging section 7.

The address generator 21 is connected to a control panel (not shown) of the operation section 2 so as to receive a tracking command and a window signal, both generated by operating the control panel. The tracking command instructs the signal-processing section 3 to control the wire drivers 4X and 4Y, such that the imaging section 7 tracks the object automatically. It is also supplied to the switches 25x and 25y, turning these switches on. The window signal designates a selected region of interest of the object, i.e., that part of the object which is the tracking target. In accordance with the tracking command and the window signal, the address generator 21 performs memory-address control. As a result, the image signals (i.e., luminance signals Y) forming a first image of the region of interest, which has been designated by the window signal, are stored into the frame memory 22.

The two-dimensional correlation circuit 23 compares the image signals stored in the frame memory 22 with the image signals produced thereafter by the CCD 12 and forming a second image of the same region of interest. Hence, the circuit 23 obtains the value of two-dimensional correlation between any image signal forming the first image and the corresponding image signal forming the second image. Thus, the two-dimensional correlation values are obtained for all image signals forming the first image, on the one hand, and all image signals forming the second image, on the other. Further, the circuit 23 determines the X-direction displacement dx between the two images and also the Y-direction displacement dy between these images. The two-dimensional correlation is carried out in accordance with the various algorithms hitherto known. Basically, it is carried out by determining the displacements which occur when the value of correlation between the two images is maximum.

The two-dimensional correlation circuit 23 is supplied with data about the region of interest designated by the window signal. In accordance with this data, it selects those of the image signals supplied from the video processor 15 via the signal-compensating device 16, which form a region including the region of interest designated by the window signal and broader than the region of interest. Then, the circuit 23 compares these selected image signals with the image signal stored in the frame memory 22, thereby obtaining the value of two-dimensional correlation between any image signal stored in the memory 22 and the corresponding image signal just supplied from the video processor 15 via the signal-compensating circuit 16.

It will now be explained, in greater detail, how the two-dimensional correlation is accomplished, with reference to FIG. 2. Assuming that the image signals stored in the frame memory 22 forms an image f1, there are obtained an Y-direction projection g1 and a X-direction projection h1.

Upon lapse of a period of time thereafter, a second image f2 is formed of the selected ones of the image signals supplied from the video processor 15 via the signal-compensating device 16. Of the second image, too, there are obtained an Y-direction projection g2 and a X-direction projection h2. As is evident from FIG. 2, a displacement dx exists between the Y-direction projections g1 and g2, and a displacement dy between the X-direction projections h1 and h2. This means that the object has moved, during said period of time, in the X and Y directions by distances proportional to the X-direction displacement dx and Y-direction displacement dy, respectively.

The two-dimensional correlation circuit 23 calculates a correlation between the projections in the two directions, thereby to determine displacements dx and dy between the two images f1 and f2. For example, square sums of the displacements between the respective projections are obtained. In this case, the two-dimensional correlation assumes a peak value at a specific point (dx, dy) in the X-Y coordinates. Then, the X-axis coordinate dx and Y-axis coordinate dy of this point correspond to the X-direction and Y-direction displacements between the images f1 and f2, respectively.

The circuit 23 performs the two-dimensional correlation on the images f1 and f2. More precisely, it processes the luminance signals Y supplied from the video processor 15 through the signal-compensating device 16, thereby generating quickly correlation signals which represent the X-direction displacement and the Y-direction displacement, both between each image formed on the imaging surface of the CCD 12 at a predetermined cycle and the image previously formed by the CCD 12 and represented by the luminance signals Y stored in the frame memory 22. The correlation signals representing the X-direction displacement are supplied to the first interpolation circuit 24x, and the correlation signals showing the Y-direction displacement are supplied to the second interpolation circuit 24y.

The first interpolation circuit 24x interpolates the correlation signals representing the X-direction displacement, thereby obtaining a correct X-direction displacement between the two images f1 and f2. Similarly, the second interpolation circuit 24y interpolates the correlation signals representing the Y-direction displacement, thereby obtaining a correct Y-direction displacement between the images f1 and f2. The data items showing the X-direction displacement and the Y-direction displacement, thus obtained, are input to the X-direction angle wire driver 4x and the Y-direction angle wire driver 4y through the switches 25x and 25y, respectively.

In accordance with the X-direction displacement, the wire driver 4x drives the X-direction angle wire 5x. Simultaneously, in accordance with the Y-direction displacement, the wire driver 4y drives the Y-direction angle wire 5y. As a result, the distal end of the insertion section 1 is moved in both the X direction and the Y direction in the plane perpendicular to the optical axis of the imaging section 7. Hence, the imaging section 7, which is located within the distal end, is moved such that its displacement with respect to the object is eliminated. Then, the CCD 12 of the section 7, now correctly positioned with respect to the object, generates image signals representing the image of the object. These signals are supplied to the A/D converter 14 and processed by the video processor 15, providing luminance signals Y and color-difference signals (R-Y) and (B-Y). The signals (R-Y) and (B-Y) are input to the NTSC signal generator 17, which the luminance signals Y are processed by the signal-compensating device 16 and supplied to the NTSC signal generator 17. The generator 17 produces NTSC TV signals from the signals Y and the signals (R-Y) and (B-Y). The TV signals are output to the image monitor (not shown).

It will be explained how the interpolation circuit 24x performs its function, with reference to FIG. 3. Let us assume that the two-dimensional correlation circuit 23 supplies the circuit 24x with three correlation signals P0, P1 and P2 which represent the X-direction displacements X0, X1 and X2 of three pixels. In this case, the correct displacement X is calculated in the following way:

[If $P0 \geq P2$]

$$X = X1 + \frac{1}{2} \cdot \frac{P0 - P2}{P0 - P1}$$

[If $P0 < P2$]

$$X = X1 - \frac{1}{2} \cdot \frac{P2 - P0}{P2 - P1}$$

This linear interpolation yields an accurate X-direction displacement between each pixel of the image f1 and the corresponding pixel of the image f2. Any other interpolation hitherto known can, of course, be employed to determine the X-direction displacement accurately.

The interpolation circuit 24y operates in a way similar to the interpolation circuit 24x, thereby to accomplish an accurate Y-direction displacement between each pixel of the image f1 and the corresponding pixel of the image f2.

As has been described, the displacement between the imaging section 7 and the object existing in a body cavity is detected from the two-dimensional correlation between any two successive images of the object formed by the section 7 which is built in the distal end of the insertion section 1 inserted in the cavity. In accordance with the displacement thus detected, the wire drivers 4x and 4y drives the angle wires 5x and 5y, moving the distal end of the section 1 such that the displacement between the section 7 and the object is eliminated. Due to this negative feedback control of the distal end of the insertion section 1, the imaging section 7 tracks the object. In other words, the positional relation between the section 7 and the object remains unchanged. The imaging section 7, taking a constant positional relation with the object, forms images of the object at regular time intervals, and the monitor display displays these images, one after another.

As is illustrated in FIG. 1, the imaging section 7 further comprises two acceleration sensors 31 and 32, which are located near the zoom lens 11 and the CCD 12, respectively. The first acceleration sensor 31 is used to detect the displacement of the zoom lens 11, whereas the second acceleration sensor 32 is used to detect the displacement of the CCD 12. More precisely, the sensor 31 detects the acceleration at which the lens 11 moves in the X direction, and also the acceleration at which the lens 11 moves in the Y direction, and the sensor 32 detects the acceleration at which the CCD 12 moves in the X direction, and also the acceleration at which the CCD 12 moves in the Y direction.

The first acceleration sensor 31, which is located near the zoom lens 11, comprises two sensor units x1 and y1 (not shown in FIG. 1). The sensor units x1 and y1 detect the vertical and horizontal displacements of the zoom lens 11, respectively. They are located such that their axes intersect at a point located at a distance r from the optical axis M of the lens 11.

The second acceleration sensor 32, which is located near the CCD 12, comprises two sensor units x2 and y2 (not shown in FIG. 1). The sensor units x2 and y2 detect the vertical and horizontal displacements of the CCD 12, respectively. These units are positioned such that their axes intersect at a point located at a distance r from the optical axis M of the CCD 12. The sensor units x2 and y2 are positioned symmetrically with respect to the sensor units x1 and y1, with respect to the optical axis of the CCD 12.

FIG. 4 is a sectional view showing an acceleration sensor unit 100 which can be used as sensor units x1, y1, x2 and y2. The acceleration sensor unit 100 is an electromagnetic induction type which comprises springs 101, a coil 102, a magnetic circuit 103, and a resistor R. The coil 102 is supported by the springs 101 which are connected to the zoom lens 11 or the CCD 12. The coil 102 is located in the magnetic circuit 103. The circuit 103 has a permanent magnet 103a. The resistor R is connected between the ends of the coil 102. When the coil 102 moves relative to the magnet 103a, due to the vibration of the imaging section 1, it generates an electromotive force. The electromotive force is output in the form of an acceleration signal through the resistor R.

As is shown in FIG. 1, a comparator 33, an integrator 34, and an actuator driver 35 are provided in the operation section 2 of the endoscope. The acceleration signals output by the sensor units x1, x2, y1 an y2, each having the structure shown in FIG. 4, are supplied to the comparator 33. The comparator 33 compares the acceleration signals output by the sensor units x1 and x2, and generates a difference signal showing the difference in level between the acceleration signals. It also compares the acceleration signals output by the sensor units y1 and y2, and produces a difference signal representative of the difference in level between the acceleration signals. The difference signals are input to the integrator 34. The integrator 34 processes these difference signals, determining the X-direction displacement between the imaging section 7 and the object and also the Y-direction displacement between the section 7 and the object. The integrator 34 outputs an X-direction displacement signal and a Y-direction displacement signal to the actuator driver 35.

An XY actuator 36 is located in the distal end portion of the insertion section 1 of the endoscope and is electrically connected to the actuator driver 35 located in the operation section 2. The XY actuator driver 35 drives the XY actuator 36 in accordance with the X-direction and Y-direction displacement signals supplied from the integrator 34. As a result, the optical positional relation between the lens 11 and the CCD 12 is corrected such that an image of the object is formed at the desired position on the imaging surface of the CCD 12. Therefore, the displacement of the imaging section 7 with respect to the object is eliminated.

As is illustrated in FIG. 5, the XY actuator 36 comprises four coils 111, 112, 113 and 114 and a support frame 115. The coils 111 to 114 are connected to the support frame 115 and magnetically coupled to the four sides of the CCD 12, respectively. When driven by the actuator driver 35 in accordance with the X-direction displacement signal, the first and second coils 111 and 112 move the CCD 12 in the X direction or the horizontal direction. When driven by the actuator 35 in accordance with the Y-direction displacement signal, the the third and fourth coils 113 and 114 move the CCD 12 in the Y direction or the vertical direction. The XY actuator 36 can have only two coils, instead of four, for moving the CCD 12 in the X direction and the Y direction, respectively.

The displacement between the imaging section 7 and the object is eliminated at high speed in accordance with the X-direction and Y-direction displacement signals which the integrator 34 generates from the signals output by the acceleration sensors 31 and 32. At the same time, as has been described, the distal end of the insertion section 1 is moved by means of angle wire drivers 4x and 4y in accordance with the correlation signals output from the two-dimensional correlation circuit 23, whereby the imaging section 7 tracks the object within the body cavity. Thus, both the displacement between the imaging section 7 and the object detected by the two-dimentional correlation and the displacement between the object and the imaging section 7 obtained from the acceleration detection, either resulting from the vibration of the section 7, are automatically eliminated, whereby the image displayed on the screen of the monitor display does not oscillate.

With reference to the flow chart of FIG. 6, it will now be explained how an operator positions the imaging section 7 with respect to the object within a body cavity, while seeing the image of the object displayed on the monitor display, i.e., the TV receiver.

First, in step S1, the operator inserts the insertion section 1 of the endoscope into the body cavity. In step S2, the operator operates the control panel, inputting a tracking command and a window signal. The tracking command turns on both switches 25x and 25y of the signal-processing section 3. The window signal designates a selected region of interest of the object, i.e., that part of the object which is the tracking target. Then, in step S3, the two-dimensional correlation circuit 23 determines the displacement of the selected region of the object with respect to the imaging section 7, and supplies correlation signals via the switches 25x and 25y to the angle wire drivers 4x and 4y. In accordance with these signals, the drivers 4x and 4y drives the X-direction angle wire 5x and the Y-direction angle wire 5y, moving the distal end of the insertion section 1, whereby the imaging section 7 tracks the object.

Step S3 will be described in detail. First, the data representing the image f1 of the region of interest, which has been designated by the window signal, is stored into the frame memory 22. Then, the two-dimensional correlation circuit 23 determines the X-direction and Y-direction displacements between the image f1 stored in the memory 22 and the next image f2 formed by the imaging section 7, and produces correlation signals representing the X-direction and Y-direction displacements between the images f1 and f2. The first interpolation circuit 24x interpolates the correlation signals showing the X-direction displacement, correcting the X-direction displacement. The second interpolation circuit 24y interpolates the correlation signals representing the Y-direction displacement, correcting the Y-direction displacement. The data items showing the X-direction displacement and the Y-direction displacement, thus obtained, are input to the X-direction angle wire driver 4x and the Y-direction angle wire driver 4y through the switches 25x and 25y, respectively. In accordance with the X-direction displacement, the wire driver 4x drives the X-direction angle wire 5x. In accordance with the Y-direction displacement, the wire driver 4y drives the Y-direction angle wire 5y. As a result, the distal end of the insertion section 1 is moved in both the X direction and the Y direction in the plane perpendicular to the optical axis of the imaging section 7. Hence, the imaging section 7, which is located within the distal end, is moved such that its displacement with respect to the selected region of the object is eliminated. Then, the CCD 12 of the section 7, now correctly positioned with respect to the object, generates image signals representing the image of the object.

The imaging section 7 is positioned by means of negative feedback control, wherein no phase control is performed, and the section 7 is moved in the direction opposite to the direction in which the section 7 has been displaced with respect to the object. In other words, phase compensation is applied to position the imaging section 7, thereby preventing a positive feedback. Therefore, even if the object moves in the opposite direction to increase the displacement between it and the section 7, while the imaging section 7 is forming an image of the object, the angle wire drives 4x and 4y drives the angles wires 5x and 5y such that the section 7 is moved in the same direction as the object, successfully tracking the object.

At the same time the imaging section 7 tracks the object as described in the preceding paragraph, the displacement between the object and the section 7 is eliminated at high speed in the specific method explained above. Hence, both the displacement detected by two-dimentional correlation and the displacement detected from the signals of the acceleration sensors 31 and 32, either resulting from the vibration of the section 7, are automatically eliminated. The image displayed on the screen of the monitor display does not oscillate. In addition, there occurs no displacement between the the selected region of the object and the imaging section 7 even while the section 7 is "frozen" at a specific position. Hence, a clear image of the object can be recorded.

In step S4, the operator inserts the insertion section 1 deeper into the body cavity, moving the imaging section 7 closer to the object, in order to have a better view of the region of interest, while seeing the image of the region on the screen of the monitor display. Next, in step S5, the operator operates the control panel, thereby inputting a new window signal designating a narrower region of the object. Then, the flow returns to step S3, in which the imaging section 7 is moved, if necessary, to track the object within the body cavity.

When the distal end of the insertion section 1 moves so close to the object that no illumination light can no longer be applied to the object, the operator pulls the section 1, thus moving the imaging section a little away from the object, allowing the light to illuminate the object. Then, in step S4, he or she operates the control panel, thereby inputting a zooming command. In accordance with this command, the zoom lens 11 is actuated, enlarging the image of the object. Since the displacement between the imaging section 7 and the object has been eliminated in step S3, the section 7 forms a high-resolution, enlarged image of that region of the object which has been designated in step S5.

As may be understood from the above, the displacement between the imaging section 7 and the object can be eliminated, no matter whether the displacement has occurred due to the motion of the object or the vibration of the section 7 being moved toward the object. This helps to enhance the operation efficiency of the endoscope remarkably.

In the imaging device described above, i.e., the first embodiment of the present invention, the acceleration sensors 31 and 32 are used to detect the displacement between the object and the imaging section 7. The acceleration sensors 31 and 32 can be dispensed with, provided that the CCD 12 is replaced by an AMI (Amplifier-Type MOS Imager). This is because the AMI forms images of an object at so high a speed that the displacement between the object and the section 7 can be determined by comparing any two consecutive images formed by the AMI.

FIG. 7 schematically illustrates an endoscope having an imaging device according to a second embodiment of the invention which has an AMI used to detect the displacement between an imaging section and an object. In FIG. 7, the same numerals denote the components identical to those illustrated in FIG. 1.

The imaging device shown in FIG. 7 is different from the device shown in FIG. 1 in several respects. First, the imaging section 7 has an AMI 18. Second, an additional address generator 43 is connected the output terminals of a two-dimensional correlation circuit 23. Third, three adders 41a, 41b and 41c are used, the adder 41a connected to the output of a signal-compensating device 16 and the adders 41b and 41c connected to a video processor 15. Fourth, three additional frame memories 42a, 42b and 42c are connected to the outputs of the adders 41a, 41b and 41c, respectively. Further, the outputs of the frame memories 42a, 42b and 42c are connected to an NTSC signal generator 17.

The AMI 18 forms images of the object at speed higher than TV rate. Hence, the displacement between an object and the imaging section 7 can be determined by comparing any two consecutive images formed by the AMI, and the displacement, thus detected, can be quickly eliminated.

The high-speed forming of images means that the AMI 18 has but a short exposure time. The shorter the exposure time, the lower the levels of the image signals the AMI 18 generates. To compensate for the levels of these image signals, the adders 41a, 41b an 41c, and the frame memories 42a, 42b and 42c are used. More precisely, the adder 41a and the frame memory 42a add the luminance signals Y the device 16 produces for each TV-rate period, forming a sum signal; the adder 41b and the frame memory 42b add the color-difference signals (B-Y) the processor 15 outputs for each TV-rate period, forming a sum signal; and the adder 41c and the frame memory 42c add the color-difference signals (R-Y) the processor 15 generates for each TV-rate period, thus forming a sum signal. The sum signals are input to the NTSC signal generator 17, which converts the sum signals into TV signals.

Meanwhile, the additional address generator 43 generates address signals from the correlation signals which are supplied from the two-dimensional correlation circuit 23 and which represent the displacement between any two consecutive images formed by the AMI 18. The address signals are supplied to the frame memories 42a, 42b and 42c. In accordance with the address signals, the frame memories 42a, 42b and 42c read the sum signals simultaneously. Hence, the sum signals are supplied to the NTSC signal generator 17 at the same time.

In the imaging device according to the second embodiment of the invention, the displacement between the object and the imaging section 7 can be fast determined by comparing any two consecutive images formed by the AMI 18, and the displacement can be eliminated at once. Moreover, since the image signals which the AMI 18 generates for each TV-rate period are added, forming sum signals, and the sum signals are simultaneously supplied from the frame memories 42a, 42b and 42c to the NTSC signal generator 17, the TV signals output by the generator 17 form an image which is not displaced from the image previously displayed by a monitor display (not shown).

As in the first embodiment (FIG. 1), the imaging section 7 can be moved quickly to track the object, eliminating the displacement between it and the object. Therefore, the section 7 forms a high-resolution image of the object, which does not oscillate when displayed on the screen of the monitor display. Seeing the image of the object, thus monitored, the operator can operate the endoscope with high efficiency.

In the imaging device described above, i.e., the first embodiment of the present invention, the XY actuator 36 moves the CCD 12, thereby correcting the optical positional relation between the lens 11 and the CCD 12 such that an image of the object is formed at the desired position on the imaging surface of the CCD 12. Also in the second embodiment (FIG. 7), an XY actuator can be used to move the AMI 18.

Figure 8:
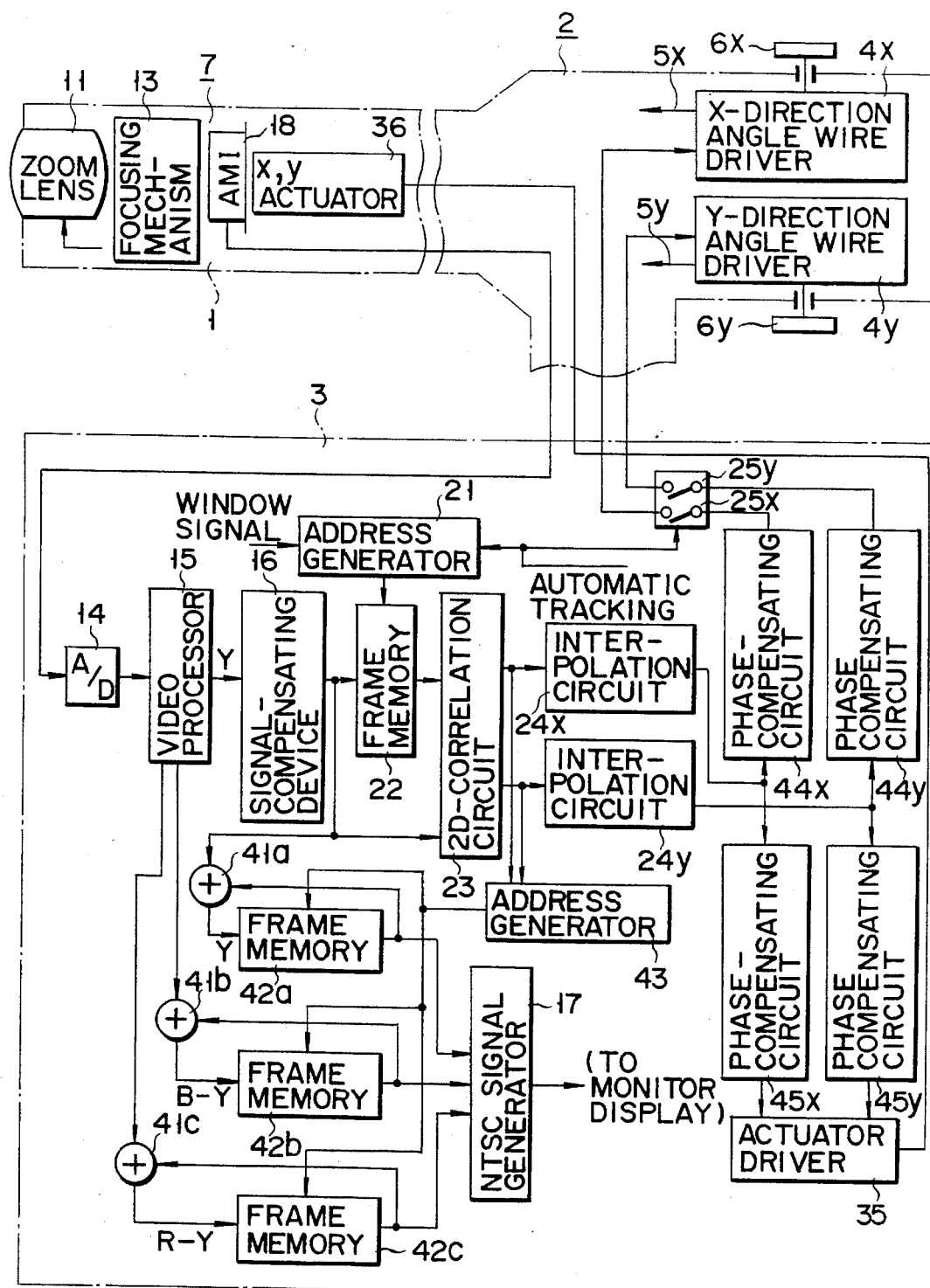
FIG. 8 is a schematic representation of an endoscope having a imaging device according to a third embodiment of the present invention.

FIG. 8 schematically illustrates an endoscope having an imaging device according to a third embodiment of the invention. The third embodiment is characterized in three respects. First, an AMI 18 is moved by an XY actuator 36. Second, phase-compensating circuits 44x and 44y are connected to the outputs of interpolation circuits 24x and 24y for controlling angle wire drivers 4x and 4y, respectively. Third, phase-compensating circuits 45x and 45y are connected, at one end, to the outputs of the interpolation circuits 24x and 24y and, at the other end, to an actuator driver 35. The phase-compensating circuits 44x and 44y have large time constants, so as to prevent a positive feedback and, hence, a backlash, even if the imaging section 7 is displaced from the object. By contrast, the phase-compensating circuits 45x and 45y have small time constants, so that the XY actuator 36 can move the AMI 18 quickly in response to the motion of the object.

Hence, the image section 7 is roughly positioned by a first feedback control system constituted by the phase-compensating circuits 44x and 44y, the angle wire drivers 4x and 4y and the angle wires 5x and 5y, and the AMI 18 is minutely positioned by a second feedback control system constituted by the phase-compensating circuits 45x and 45y, the actuator driver 35 and the XY actuator 36. As a result, the displacement between the object and the imaging section 7 can effectively eliminated, whereby the image of the object displayed on a monitor display (not shown) does not oscillate.

Figure 9:
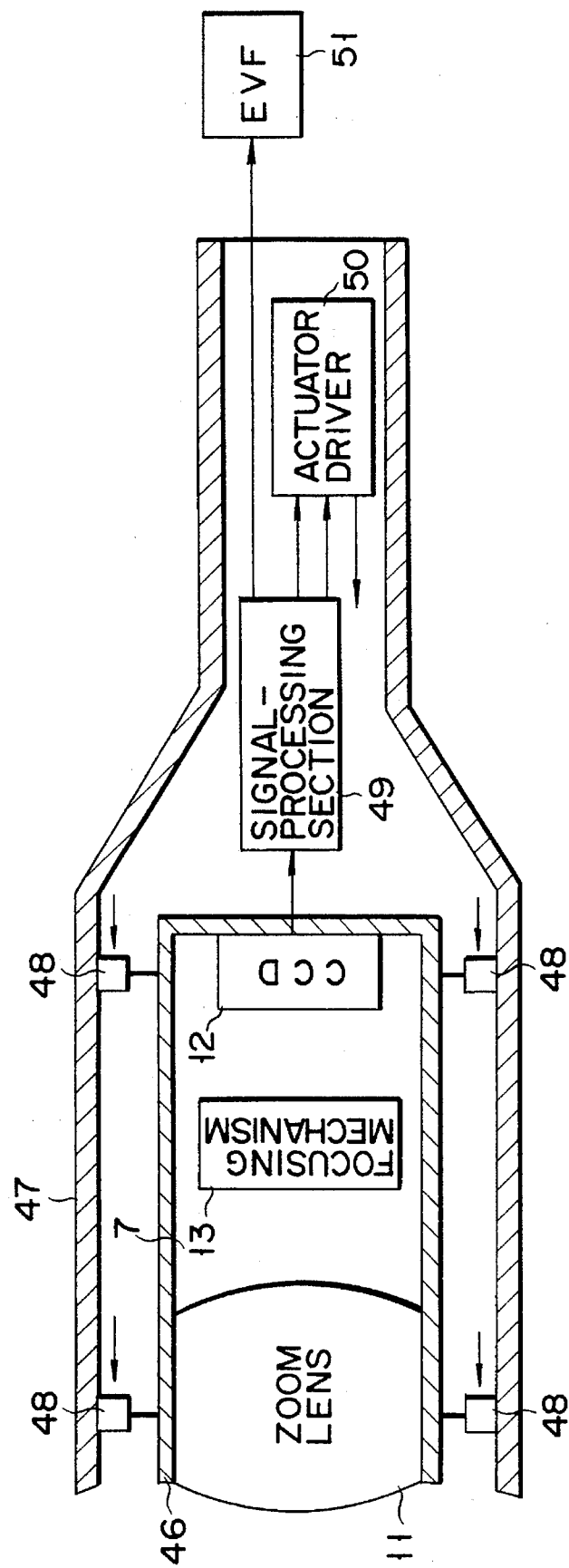
FIG. 9 schematically shows a hand-held microscope having an imaging device according to a fourth embodiment of this invention.

FIG. 9 schematically shows a hand-held microscope having an imaging device according to a fourth embodiment of this invention. In this figure, the same numerals designate the same components as those shown in FIG. 1.

The imaging device shown in FIG. 9 is characterized in that the an imaging section is moved in accordance with motion vectors representing how fast and in which direction the image of an object is moving.

As is illustrated in FIG. 9, the hand-held microscope comprises an inner housing 46, an imaging section 7 provided in the inner housing 46, an outer housing 47, actuators 48 suspending the inner housing 46 within the outer housing 47, a signal-processing section 49 located in the outer housing 47, an actuator driver 50 located in the outer housing 47, and an EVF (Electronic View Finder) 51. When driven by the driver 50, the actuators 48 move the inner housing 46 such that the imaging section 7 is directed in any desired direction. The signal-processing section 49 supplies the EVF 51 with the image signals output by the CCD 12 of the imaging section 7, and processes these image signals, thereby generating displacement signals representing the X-direction and Y-direction displacements between the section 7 and an object. The actuator driver 50 drives the actuators 48 in accordance with the displacement signals supplied from the signal-processing section 49. The EVF 51 forms the image of the object from the image signals supplied from the signal-processing section 49. An operator can see this image.

Figure 10:
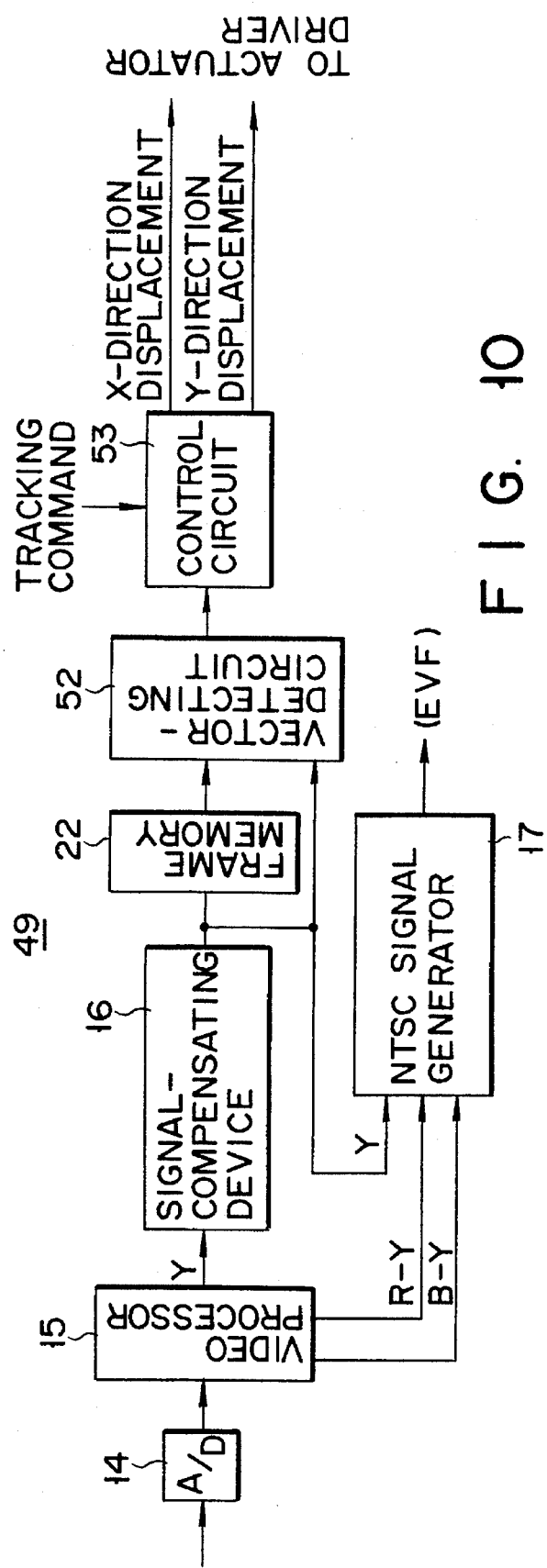
FIG. 10 is a block diagram showing the signal-processing section of the device illustrated in FIG. 9.
Figure 11:
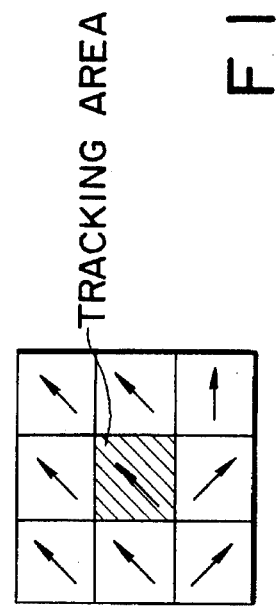
FIG. 11 schematically represents a tracking area, explaining how the signal-processing section detect the motion of an image.

As shown in FIG. 10, the signal-processing section 49 comprises an A/D converter 14, a video processor 15, a signal-compensating device 16, a frame memory 22, an NTSC signal generator 17, a vector-detecting circuit 52, and a control circuit 53. The A/D converter 14, the video processor 15, the device 16, the frame memory 22, and the NTSC signal generator 17 are of the same types as those incorporated in the imaging device shown in FIG. 1. The vector-detecting circuit 52 compares any two images of the object which the CCD 12 have formed sequentially, thereby to determine how fast and in which direction the image of the object is moving. FIG. 11 schematically shows motion vectors and a tracking area (i.e., the center square), explaining how the circuit 52 detects the motion of the image. The motion vectors detected by the circuit 52 are input to the control circuit 53. The control circuit 53 controls the actuators 48 in accordance with the motion vectors and the tracking command input by operating a control panel (not shown).

Figure 12A:
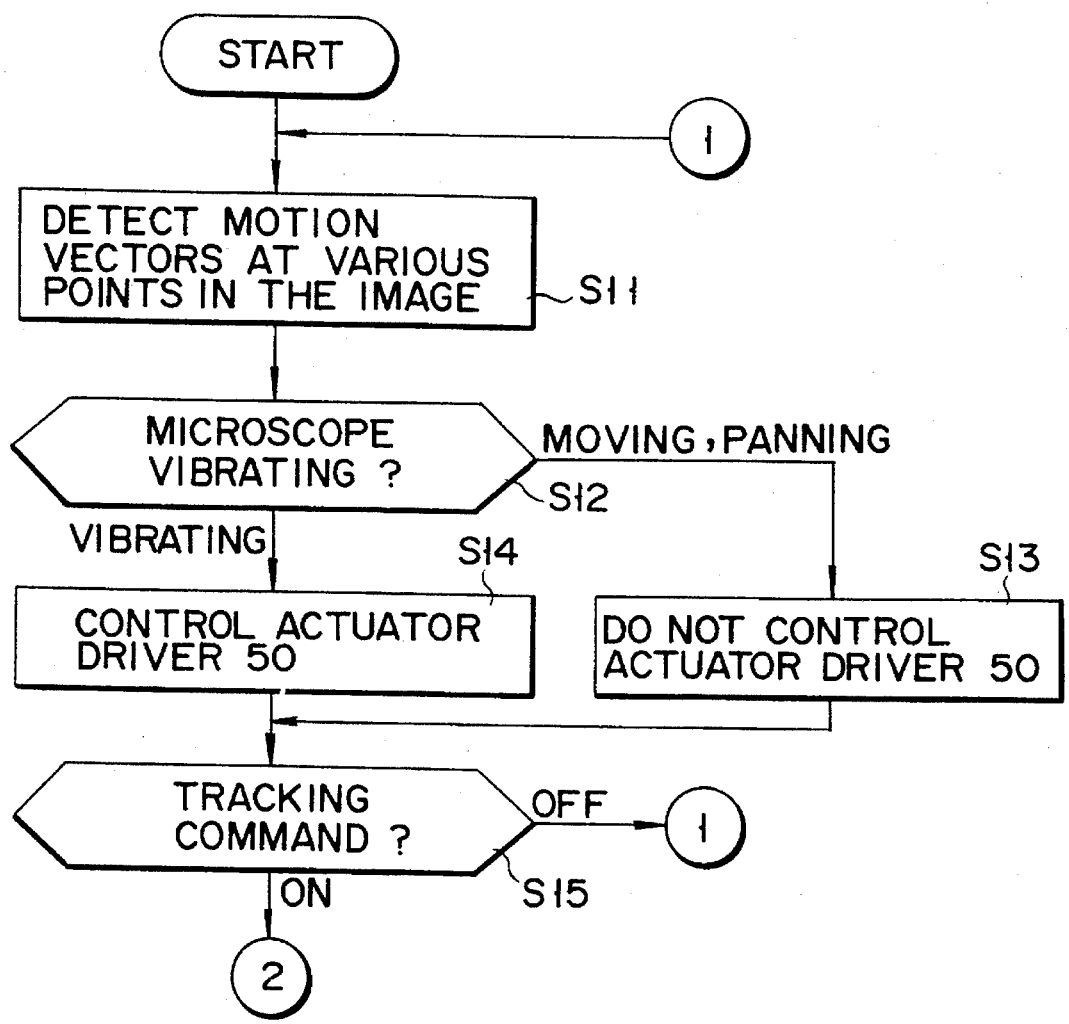

The operation of the imaging device shown in FIG. 9 will now be explained, with reference to the flow chart of FIGS. 12A and 12B.

First, the operator directs the microscope to an object of photography. It is desirable that the zoom lens 11 be set at an wide angle. The vibration of the microscope is compensated until the object is caught in the central of the tracking area. In order to distinguish this vibration compensation from panning, the signal-processing section 49 operates as follows:

First, in step S11, the vector-detecting circuit 52 detects motion vectors at all pixels of the image of the object, by comparing any two images of the object which the CCD 12 have formed sequentially. In step S12 it is determined whether the microscope is vibrating or not. If the vectors much differ in direction, it is determined that not only the microscope, but also the object is moving. In this case, the flow goes to step S13, in which the control circuit 53 does not control the actuator driver 50. If the vectors are substantially identical in direction for a time longer than a period predetermined in accordance with, for example, the focal distance of the zoom lens 11, then it is determined that panning is being performed, in which case the flow goes to step S13. If the vectors are almost the same in direction for a time equal to or shorter than the predetermined period, it is determined that the microscope is vibrating. In this case, the flow goes to step S14, in which the control circuit 53 controls the actuator driver 50.

Namely, the control circuit 53 operates in the following manner:

1. It does not control the driver 50 if the motion vectors much differ in direction, assuming that the object is moving much.
2. It does not control the driver 50 if the vectors are substantially identical in direction for a long time, assuming that panning is being performed.
3. It controls the driver 50 if the vectors are substantially identical in direction but for a short time, assuming that the microscope is vibrating.

When the operator catches the image of the object in the tracking area, he or she inputs a tracking command. In step S15 it is determined whether or not a tracking command has been input. If YES, the flow goes to step S16. If NO, the flow returns to step S11. The image of the object, which the CCD 12 forms the moment the tracking command is input, is stored into the frame memory 22. In step S16, the vector-detecting circuit 52 detects motion vectors at all pixels forming the image of the object, by comparing the image stored in the memory 22 with the next image formed by the CCD 12. As long as the tracking command is input, the control circuit 53 controls the actuator driver 50, in step S17. If necessary, the zoom lens 11 is operated in step S18, thus lengthening the focal distance, thereby to enlarge the image of the object. Once the focal distance is changed, the contents of the frame memory 22 is updated.

Whether the object moves, or the microscope is vibrated, the imaging section 7 can track the object as the actuators 48 are driven by the actuator driver 50. This is because the driver 50 is controlled in accordance with the motion vectors detected in the tracking area by means of the vector-detecting circuit 52.

However, when the object moves too much or too fast, the actuators 48 can no longer move the imaging section 7 such that the section 7 tracks the object well. In step S19, it is determined whether the automatic tracking is impossible. If NO, the flow returns to step S16. If YES, the flow goes to step S20, in which the image of the object moves out of the tracking area. Thus, in step S21, the operator stops the automatic tracking. Then, steps S11 to S15 (a vibration correcting operation) are repeated. The operator moves the microscope to catch the image of the object in the tracking area. If necessary, he or she sets the zoom lens 11 at the wide angle. Upon catching the image of the object in the tracking area, he or she inputs a tracking command. Then, steps S16 to S21 (a tracking operation) are repeated, whereby the imaging section 7 tracks the object which is moving.

As has been described, the signal-processing section 49 controls the actuator driver 50 in accordance with the motion vectors detected at all pixels forming the image of the object, until the operator catches the image in the tracking area and inputs a tracking command. Once a tracking command is input, the section 49 controls the actuator driver 50 in accordance with the motion vectors detected in the tracking area. As a result of this, the actuator 48 moves the imaging section 7, such that the section 7 tracks the object. Hence, the image of the object is clear and automatically caught in the tracking area.

Since the imaging section 7 keeps tracking the object after the operator has input the tracking command, it suffices to input a zooming command in order to actuate the zooming lens 11, so that the image of the object is enlarged. In addition, since the EVF 51 is located outside the outer housing 47, the microscope can take any position desired at any place. Needless to say, the EVF 51 can be formed integral with the microscope.

In the fourth embodiment shown in FIG. 9, the imaging section 7 is located in the inner housing 46 and is moved, in its entirety, by the actuators 48. Instead, only the zoom lens 11 or the CCD 12 can be moved by an actuator. Further, as in the second and third embodiments, the image stored in each frame memory is read, starting at the address of the frame memory which has been specified in accordance with the displacement between the imaging section 7 and the object. Still further, this method of reading the image from each frame memory can be combined with the technique of moving only the lens 11 or the CCD 12 by means of the actuator.

Figure 13:
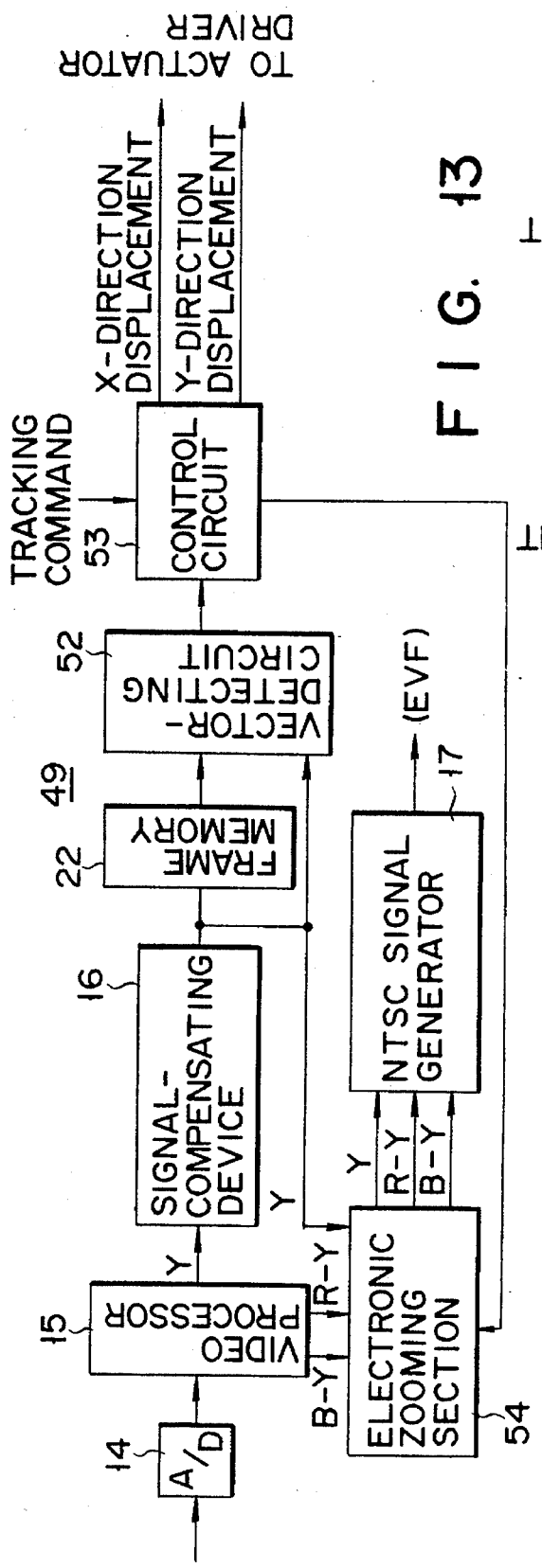
FIG. 13 is a block diagram showing the signal-processing section incorporated in a hand-held microscope having an imaging device according to a fifth embodiment of the present invention.

FIG. 13 is a block diagram showing the signal-processing section 49 incorporated in an imaging device according to a fifth embodiment of the present invention. The imaging device is characterized in that the imaging section is moved not only in the vertical and horizontal directions but also back and forth, so that the image of an object is seen at the same position and in the same size in the tracking operation of the object.

Figure 14B:
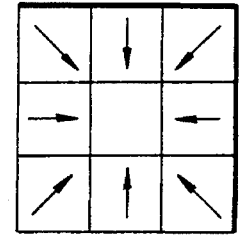
FIGS. 14A and 14B are diagrams explaining how motion vectors change at the each pixel forming an image when the image is enlarged or reduced.
Figure 14A:
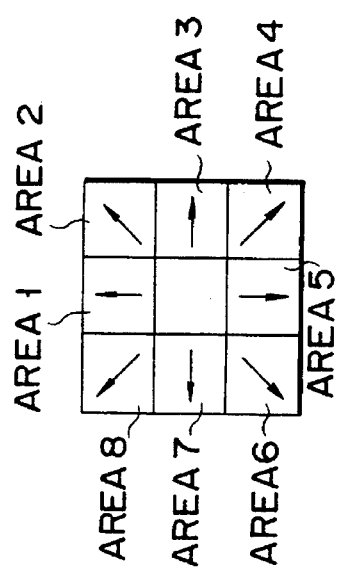

As can be understood from FIG. 13, the signal-processing section 49 is identical to the section 49 shown in FIG. 10, except that it has an electronic zooming section 54. The zooming section 54 comprises a RAM and can enlarge and reduce any image formed by the CCD (not shown). When the section 54 enlarges the image, the motion vectors at all pixels of the image change in magnitude, as is illustrated in FIG. 14A. When the section 54 reduces the image, the motion vectors change in magnitude, as is illustrated in FIG. 14B. The image-enlargement or -reduction ratio α is detected from the changes of these vectors. More specifically, the ratio α can be determined from the X-axis components of adjacent vectors, as will be explained with reference to FIGS. 15A and 15B.

Figures 15A, 15B:
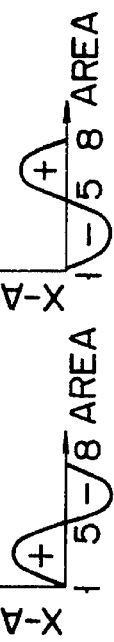
FIGS. 15A and 15B are graphs representing what values the X components of the motion vectors shown in FIGS. 14A and 14B have in various areas 1 to 8.

FIG. 15A is a graph showing the values which the X-axis components of the vectors have in areas 1 to 8 specified in FIG. 14A. FIG. 15B is a graph representing the values which the X components of the vectors have in areas 1 to 8 specified in FIG. 14B. As can be under stood from FIGS. 15A and 15B, the polarity of the X-axis component of any vector depends on whether the image is enlarged or reduced, and the absolute value thereof is proportional to the image-enlargement/reduction ratio α. Hence, the ratio α can be determined from the absolute value of the X-axis components of the motion vectors.

If the image of the object is enlarged or reduced and also makes a parallel movement, the vectors of the parallel movement is added to the motion vectors of the enlargement or reduction. The sum of the vectors resulting from the image enlargement or reduction can be regarded as zero. In the case where the image includes no moving objects, the sum of the motion vectors at all pixels forming the image is equal to that of the vectors resulting from the parallel movement of the image. Therefore, the image-enlargement/reduction ratio α can be obtained by the following method. First, the vectors of the parallel movement are detected from the sum of the motion vectors at all pixels forming the image. Next, the vector of parallel movement are subtracted from the motion vectors at the corresponding pixel, thereby finding motion vectors resulting from the image enlargement or reduction only. Then, the changes in the X-axis components of these motion vectors are determined. Finally, the the image-enlargement/reduction ratio α is detected from the changes thus determined.

In the case where the image includes a moving object, the sum of the motion vectors at the pixels forming the image is not equal to that of the vectors resulting from the parallel movement of the image. The X-axis component of each vector, which corresponds to those shown in FIGS. 15A and 15B, has a value different from the value it takes when the image is either enlarged or reduced. Hence, no accurate image-enlargement/reduction ratios &A can be obtained, and it is thus determined that the image has been neither enlarged nor reduced.

With reference to FIG. 16 it will be explained more specifically how the signal-processing section 49 obtains the image-enlargement/reduction ratio α. First, the motion vectors at all pixels forming the image are supplied to a mean vector detector 55, and also to a subtracter 56. The detector 55 finds the mean value of these motion vectors, i.e., a mean motion vector. The mean motion vector is input to the subtracter 56. The subtracter 56 subtracts the mean motion vector from each motion vector, and supplies the difference between the mean motion vector and each motion vector, to a X-axis component detector 57. From this difference the detector 57 detects the X-axis component Vx(i) of each motion vector, where i=1 to 8 and designates the area of the image. The X-axis component Vx(i) is input to a multiplier 58. A function h(i), which has been obtained by sampling a sine function as is illustrated in FIG. 17 and is used to determine whether the image has been enlarged or reduced, is also input to the multiplier 58. The multiplier 58 multiplies the X-axis component Vx(i) by the function h(i). The product Vx(i) h(i), this obtained, is supplied to an adder 59. The adder 59 accumulates the products Vx(i) h(i) obtained for all motion vectors, forming a value E which is given as follows:

$$E = \Sigma V_x(i) h(i)$$

The value E is supplied to a discriminator 60. From the value E the discriminator 60 obtains the image-enlargement/reduction ratios α. To be more specific, when $E \leq \epsilon$ ($\epsilon$ is an appropriate constant), the discriminator 60 determines that the image includes a moving object or the image has not been enlarged or reduced, and outputs the data of α=0. When $E > \epsilon$, the discriminator 60 determines that the image has been enlarged, and outputs the data of α=1+(E/L), where L is the average distance between the center of the image and any area of the image. When $E < -\epsilon$, the discriminator 60 determines that the image has been reduced, and outputs the data of α=1− (E/L).

Figure 18:
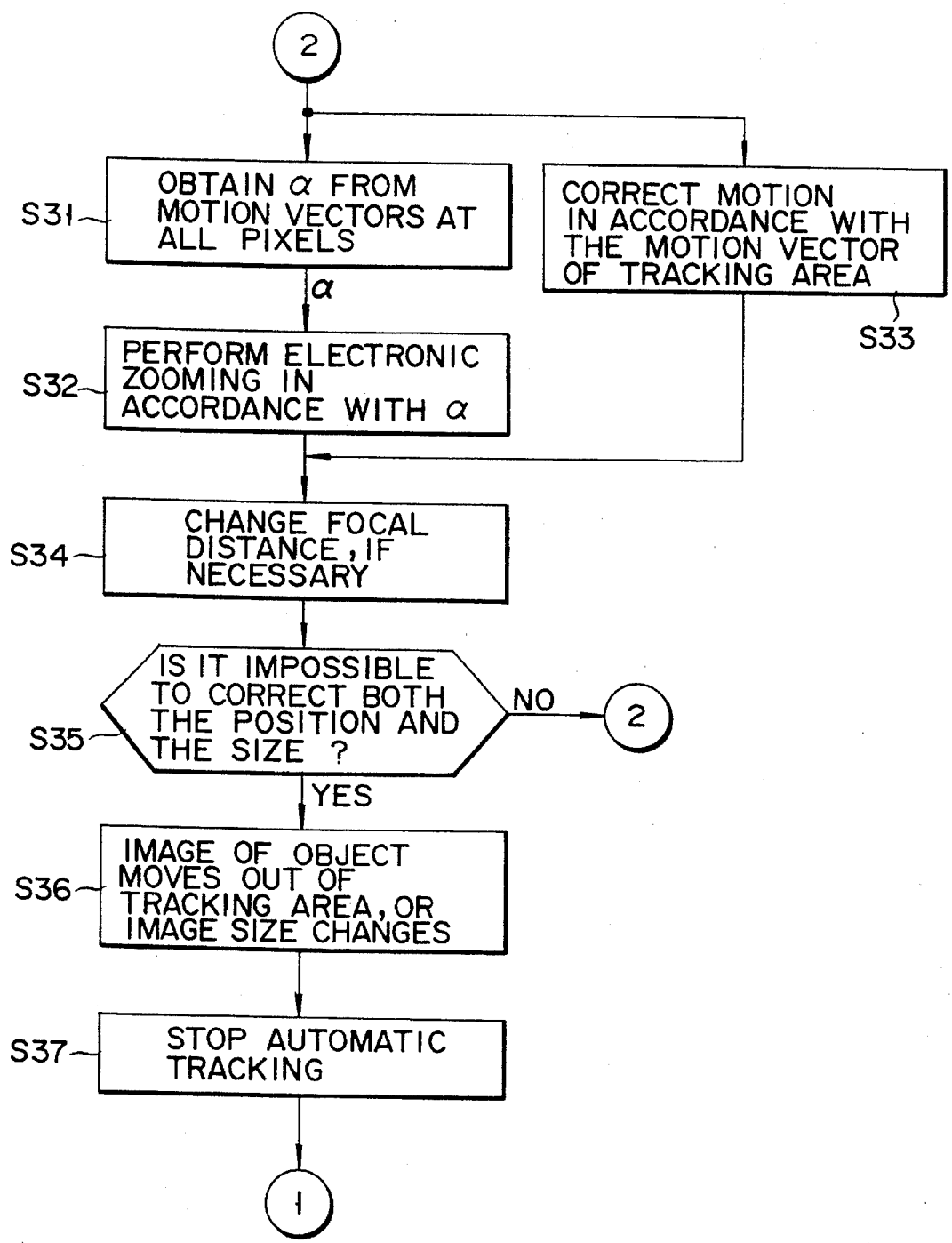
FIG. 18 is a flow chart explaining the operation of the imaging device illustrated in FIG. 13.

With reference to the flow chart of FIG. 18, it will now be explained how the control circuit 53 shown in FIG. 13 operate so that the imaging section 7 tracks the object. To eliminate the displacement between the object and the section 7, resulting from the vibration of the microscope, the same steps as steps (the vibration correcting operation) S11 to S15 (FIG. 12A) are performed. Then, the operator moves the microscope to catch the image of the object in the tracking area. Upon catching the object in the tracking area, he or she inputs a tracking command. Then, the imaging section 7 tracks the object which is moving. The image, which the CCD 12 forms the moment the tracking command is input, is stored into the frame memory 22 (FIG. 13). Thereafter, the vector detector 52 compares any two images formed sequentially by the CCD 12, thereby detecting the motion vectors at all pixels forming the image. In step S31, the signal-processing section 49 obtains the image-enlargement/reduction ratio α, as has been explained with reference to FIG. 16. In step S32, the control circuit 53 controls the electronic zooming section 54, such that the ratio α is corrected. Simultaneously, in step S33, the circuit 53 controls the actuators 48, thereby moving the imaging section 7 and eliminating the displacement between the object and the section 7. Since the circuit 53 controls both the imaging section 7 and the electronic zooming section 54, the operator can see the image of the same size located at the same position.

In step S34, the zoom lens 11 is operated, if necessary, thus changing the focal distance of the lens 11 in order to enlarge or reduce the image. The data representative of the image, thus enlarged or reduced, is stored into the frame memory 22. Then, the control circuit 53 controls the imaging section 7 in accordance with the image stored in the memory 22, whereby the imaging section 7 automatically tracks the object (the tracking operation).

In step 35 it is determined whether it is impossible to correct both the position of the image and the size thereof. If NO, the flow returns to step S31. If YES, the flow goes to step S36, in which the image moves out of the tracking area, or becomes larger or smaller. In step 37, the operator stops the automatic tracking. Then, the flow returns to step S11 (FIG. 12A). Thereafter, the operator directs the microscope to an object of photography to catch the image of the object in the center of the tracking area. When he or she catches the image of the desired size in the tracking area, he or she inputs a tracking command. Then, the imaging section 7 automatically tracks the object.

As has been described above, the imaging section 7 is controlled to eliminate the displacement between it and the object which has resulted from the vibration of the microscope, until the operator inputs a tracking command. Further, both the size and position of the image are corrected after the tracking command has been input. Therefore, the operator can easily catch the image of the object, which is clear and of the same size as before and is located at the same position in the tracking area as before.

In the fifth embodiment (FIG. 13), the electronic zooming section 54 is used to correct the size of the image. Nonetheless, the section 54 can be dispensed with. In the case where the section 54 is not used, it suffices to operate the zoom lens 11 to correct the size of the image. Alternatively, both the zoom lens 11 and the section 54 can be operated. If the lens 11 and the section are operated, the size of the image can be corrected over a broader range.

With the fifth embodiment it is possible to detect the angle through the image has been rotated, and to control the electronic zooming section 54 or operate the imaging section 7 in accordance the angle of rotation, thereby to positioning the image correctly. Further, any focusing member other than the focusing mechanism 13 and the signal-compensating device 16, in order to form an image of a great focal depth.

The present invention is not limited to the first to fifth embodiments described above which are designed for use in endoscope and hand-held microscopes. The invention can also be applied to any imaging device for use in a microscope or the like, which comprises an imaging section and means for eliminating the displacement between the imaging section relative and an object, which has resulted from the vibration of the microscope or the like.

As has been described, the imaging device according to the invention comprises an imaging section and means for compensating any displacement between the imaging section relative and an object, resulting from the vibration of the apparatus including the imaging device. Hence, it is useful in particular when it is built in an electronic still camera which is used for achieve macrophotography or telephotography.

Any embodiment described above is designed to compensate for the displacement of the imaging section 7 in both the X direction and the Y direction. In the case where the section 7 is rotated, unavoidably rotating the image formed on the image-forming surface of the section 7, it suffices to rotate the CCD 12 or the AMI 18 in the same direction by the same angle, or to use a prism system, thereby to compensate for the rotation of the imaging section 7. Such a rotational displacement can be determined from the displacements detected by the acceleration sensors 31 and 32 or from the positional relation between any two images of the object the imaging section 7 has formed one immediately after the other. More precisely, the rotational displacement is obtained from the X- and Y-direction displacements of the two images, then the rotational displacement is eliminated, and finally the X- and Y-direction displacements are eliminated. A sensor designed can be used for exclusively detecting the rotational displacement between the images, and either the CCD 12 or the AMI 18 can be rotated in accordance with the rotational displacement thus detected.

Furthermore, the signal-processing section 3 and the imaging section 7 can be modified in various ways.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An imaging device comprising:

an imaging unit including an imaging element for electronically imaging an object and optical means for forming an image of the object on an imaging plane of the imaging element;

displacement-calculating means for calculating the displacement between the object and the imaging unit, on the basis of relationships among images of the object which are sequentially formed on the imaging unit; and displacement means for displacing the imaging unit, said displacement means including:

first displacement-correcting means for mechanically correcting a positional displacement among the images of the object which are formed on the imaging element, by moving the imaging element and the optical means together in one direction in a plane perpendicular to an optical axis of the optical means, whereby those movements of the object which would vary optical position relationships among the images of the object formed on the imaging element are corrected in accordance with the displacement calculated by the displacement-calculating means; and second-displacement-correcting means for correcting those movements of the imaging unit which would vary the optical position relationships among the images of the object formed on the imaging element, in accordance with the displacement calculated by the displacement-calculating means;

wherein said second displacement-correcting means mechanically displaces at least one of the imaging element and the optical means of the imaging unit, such that the imaging element and the optical means are displaced relative to each other in the plane perpendicular to the optical axis of the optical means;

wherein said optical means includes an imaging optical lens, and wherein said second displacement-correcting means includes a displacing mechanism section, located inside the imaging unit, for varying the optical position relationships which the imaging optical lens and the imaging plane of the imaging element have with reference to the object; and wherein said displacement means further includes phase-compensating means for driving the displacing mechanism section by high-speed phase compensation.

2. An imaging device according to claim 1, wherein:

said displacement-calculating means detects amounts of X- and Y-direction displacements of the image of the object at a plurality of positions within the imaging plane; and said displacement means corrects a displacement in accordance with the amounts of X- and Y-direction displacements detected by the displacement-calculating means.

3. An imaging device comprising:

an imaging unit including an imaging element for electronically imaging an object and optical means for forming an image of the object on an imaging plane of the imaging element;

displacement-calculating means for calculating the displacement between the object and the imaging unit, on the basis of relationships among images of the object which are sequentially formed on the imaging unit; and displacement means for displacing the imaging unit, said displacement means including:

first displacement-correcting means for mechanically correcting a positional displacement among the images of the object which are formed on the imaging element, by moving the imaging element and the optical means together in one direction in a plane perpendicular to an optical axis of the optical means, whereby those movements of the object which would vary optical position relationships among the images of the object formed on the imaging element are corrected in accordance with the displacement calculated by the displacement-calculating means; and second-displacement-correcting means for correcting those movements of the imaging unit which would vary the optical position relationships among the images of the object formed on the imaging element, in accordance with the displacement calculated by the displacement-calculating means;

wherein said displacement-calculating means detects how an image of the object is displaced from the imaging unit at a plurality of positions within the imaging plane, and said imaging device further comprising:

magnification-changing means for changing a magnification of an object image signal supplied from the imaging unit, and display signal-generating means for generating a display signal on the basis of the object image signal whose magnification is changed by the magnification-changing means.

4. An imaging device according to claim 3, wherein:

said displacement-calculating means detects amounts of X- and Y-direction displacements of the image of the object at a plurality of positions within the imaging plane; and said displacement means corrects a displacement in accordance with the amounts of X- and Y-direction displacements detected by the displacement-calculating means.

5. An imaging device according to claim 3, wherein said optical means includes an imaging optical lens, and wherein said second displacement-correcting means includes a displacing mechanism section, located inside the imaging unit, for varying the optical position relationships which the imaging optical lens and the imaging plane of the imaging element have with reference to the object.

6. An imaging device according to claim 5, wherein said displacement means further includes phase-compensating means for driving the displacing mechanism section by high-speed phase compensation.

7. An imaging device according to claim 3, wherein said optical means includes an imaging optical lens, and wherein said second displacement-correcting means includes:

a displacement sensor, located inside the imaging unit, for detecting a displacement within the imaging unit; and a displacing mechanism section, located inside the imaging unit, for varying the optical position relationships which the imaging optical lens and the imaging plane of the imaging element have with reference to the object, in accordance with the displacement detected by the displacement sensor.

8. An imaging device according to claim 7, wherein said displacement means further includes phase-compensating means for driving the displacing mechanism section by high-speed phase compensation.

9. An imaging device according to claim 3, wherein said second displacement-correcting means electrically controls the imaging element such that the positions of the images formed on the imaging element are displaced relative to one another in the plane perpendicular to the optical axis of the optical means.

10. An imaging device according to claim 9, wherein said second displacement-correcting means includes:

a memory for storing pixel signals produced by the imaging unit; and address control means for controlling a read address of the memory in accordance with the displacement calculated by the displacement-calculating means.

11. An imaging device according to claim 3, wherein said displacement means displaces the imaging unit in such a manner as to correct a displacement by use of displacements at a plurality of positions within the imaging plane in a case where an object tracking command is not issued, and displaces the imaging unit in such a manner as to correct a displacement by use of a displacement at a specific position within the imaging plane in a case where the object tracking command is issued.

12. An imaging device according to claim 3, wherein said displacement means further includes imaging unit-positioning means for positioning the imaging unit with reference to the object by performing negative feedback control on the basis of an output from the first displacement-correcting means.

13. An imaging device according to claim 3, wherein said displacement means further includes means for determining a displacement type on the basis of said plurality of displacements which the displacement-calculating means detects at said plurality of positions of the imaging plane with respect to the image of the object, said imaging unit being displaced in accordance with the displacement type determined by the displacement type-determining means.

14. An imaging device according to claim 3, wherein said displacement means further includes magnification-calculating means for calculating the magnification of an object image signal in accordance with said plurality of displacements which the displacement-calculating means detects at said plurality of positions of the imaging plane with respect to the image of the object, said magnification-calculating means changing the magnification of the image of the object in accordance with the magnification calculated by the magnification-calculating means.

15. An imaging device according to claim 3, wherein said displacement means further includes switching means for selecting one of the first and second displacement-correcting means.

16. An imaging device according to claim 1, wherein said optical means includes an imaging optical lens, and wherein said second displacement-correcting means includes:

a displacement sensor, located inside the imaging unit, for detecting a displacement within the imaging unit; and a displacing mechanism section, located inside the imaging unit, for varying the optical position relationships which the imaging optical lens and the imaging plane of the imaging element have with reference to the object, in accordance with the displacement detected by the displacement sensor.

17. An imaging device according to claim 16, wherein said displacement means further includes phase-compensating means for driving the displacing mechanism section by high-speed phase compensation.

18. An imaging device according to claim 1, wherein said second displacement-correcting means electrically controls the imaging element such that the positions of the images formed on the imaging element are displaced relative to one another in the plane perpendicular to the optical axis of the optical means.

19. An imaging device according to claim 18, wherein said second displacement-correcting means includes:

a memory for storing pixel signals produced by the imaging unit; and address control means for controlling a read address of the memory in accordance with the displacement calculated by the displacement-calculating means.

20. An imaging device according to claim 1, wherein said displacement means displaces the imaging unit in such a manner as to correct a displacement by use of displacements at a plurality of positions within the imaging plane in a case where an object tracking command is not issued, and displaces the imaging unit in such a manner as to correct a displacement by use of a displacement at a specific position within the imaging plane in a case where the object tracking command is issued.

21. An imaging device according to claim 1, wherein said displacement means further includes imaging unit-positioning means for positioning the imaging unit with reference to the object by performing negative feedback control on the basis of an output from the first displacement-correcting means.

22. An imaging device according to claim 1, wherein said displacement-calculating means detects how an image of the object is displaced from the imaging unit at a plurality of positions within the imaging plane, and said imaging device further comprising:

magnification-changing means for changing a magnification of an object image signal supplied from the imaging unit; and display signal-generating means for generating a display signal on the basis of the object image signal whose magnification is changed by the magnification-changing means.

23. An imaging device according to claim 22, wherein said displacement means further includes means for determining a displacement type on the basis of said plurality of displacements which the displacement-calculating means detects at said plurality of positions of the imaging plane with respect to the image of the object, said imaging unit being displaced in accordance with the displacement type determined by the displacement type-determining means.

24. An imaging device according to claim 22, wherein said displacement means further includes magnification-calculating means for calculating the magnification of an object image signal in accordance with said plurality of displacements which the displacement-calculating means detects at said plurality of positions of the imaging plane with respect to the image of the object, said magnification-calculating means changing the magnification of the image of the object in accordance with the magnification calculated by the magnification-calculating means.

25. An imaging device according to claim 22, wherein:

said displacement means further includes displacement-detecting means for obtaining a parallel-movement component and a magnification component of an object image signal in accordance with said plurality of displacements which the displacement-calculating means detects at said plurality of positions within the imaging plane with respect to the image of the object;

said imaging unit is displaced such that the parallel-movement component of the object image signal is moved in accordance with the parallel-movement component supplied from the displacement-detecting means; and said magnification-changing means changes the magnification of the object image signal in accordance with the magnification component supplied from the displacement-detecting means.

26. An imaging device according to claim 1, wherein said displacement means further includes switching means for selecting one of the first and second displacement-correcting means.

27. An electronic endoscope apparatus comprising:

an insertion section which is inserted into a body cavity, said insertion section having a distal end in which an imaging unit is incorporated, said imaging unit including an imaging element for electronically imaging an object and optical means for forming an image of the object on an imaging plane of the imaging element;

an operation section for operating the distal end of the insertion section to obtain a desired image of the object; and a signal processing section for processing an object image signal which is output from the imaging unit incorporated in the distal end of the insertion section;

said operation section including displacement-calculating means for calculating the displacement between the object and the imaging unit, on the basis of relationships among images of the object which are sequentially formed on the imaging unit;

said operation section including:

first displacement-correcting means for mechanically correcting a positional displacement among the images of the object which are formed on the imaging element, by moving the imaging element and the optical means together in one direction in a plane perpendicular to an optical axis of the optical means, whereby those movements of the object which would vary optical position relationships among the images of the object formed on the imaging element are corrected in accordance with the displacement calculated by the displacement-calculating means, and second displacement-correcting means for correcting those movements of the imaging unit which would vary the optical position relationships among the images of the object formed on the imaging element, in accordance with the displacement calculated by the displacement-calculating means, an angle wire connected to the distal end of the insertion section, and a driving section for driving the angle wire, and said first displacement-correcting means displaces the imaging unit by operating the driving section.

28. An electronic endoscope apparatus according to claim 27, wherein:

said displacement-calculating means detects amounts of X- and Y-direction displacements of the image of the object at a plurality of positions within the imaging plane; and said displacement means corrects a displacement in accordance with the amounts of X- and Y-direction displacements detected by the displacement-calculating means.

29. An electronic endoscope apparatus according to claim 27, wherein said second displacement-correcting section mechanically displaces at least one of the imaging unit and the optical means such that the imaging element and the optical means are displaced relative to each other in the plane perpendicular to the optical axis of the optical means.

30. An electronic endoscope apparatus according to claim 29, wherein said optical means includes an imaging optical lens, and wherein said second displacement-correcting means includes a displacing mechanism section, located inside the imaging unit, for varying the optical position relationships which the imaging optical lens and the imaging plane of the imaging element have with reference to the object.

31. An electronic endoscope apparatus according to claim 30, wherein:
   said displacement mechanism section includes an actuator for displacing the imaging element in X- and Y-directions;
   said operation section includes an actuator driving section for driving the actuator; and
   said second displacement-correcting means displaces the imaging element by operating the actuator driving section.

32. An electronic endoscope apparatus according to claim 30, wherein said displacement means further includes phase-compensating means for driving the displacing mechanism section by high-speed phase compensation.

33. An electronic endoscope apparatus according to claim 29, wherein said optical means includes an imaging optical lens, and wherein said second displacement-correcting means includes:
   a displacement sensor, located inside the imaging unit, for detecting a displacement within the imaging unit; and
   a displacing mechanism section, located inside the imaging unit, for varying the optical position relationships which the imaging optical lens and the imaging plane of the imaging element have with reference to the object, in accordance with the displacement detected by the displacement sensor.

34. An electronic endoscope apparatus according to claim 33, wherein:
   said displacement mechanism section includes an actuator for displacing the imaging element in X- and Y-direction;
   said operation section includes an actuator driving section for driving the actuator; and
   said second displacement-correcting means displaces the imaging element by operating the actuator driving section.

35. An electronic endoscope apparatus according to claim 33, wherein said displacement means further includes phase-compensating means for driving the displacing mechanism section by high-speed phase compensation.

36. An electronic endoscope apparatus according to claim 27, wherein said second displacement-correcting means electrically controls the imaging element such that the positions of the images formed on the imaging element are displaced relative to one another in the plane perpendicular to the optical axis of the optical means.

37. An electronic endoscope apparatus according to claim 36, wherein said second displacement-correcting means includes:
   a memory for storing pixel signals produced by the imaging unit; and
   address control means for controlling a read address of the memory in accordance with the displacement calculated by the displacement-calculating means.

38. An electronic endoscope apparatus according to claim 37, wherein:
   said imaging element is a high-speed imaging element capable of imaging an object at high speed; and
   said second displacement-correcting means includes:
      accumulating/adding means for accumulating pixel signals produced by the high-speed imaging unit and adding the pixel signals together;
      a memory for storing pixel signals obtained by the accumulating/adding means; and
      address control means for controlling a read address of the memory in accordance with the displacement calculated by the displacement-calculating means.

39. An electronic endoscope apparatus according to claim 27, wherein said displacement means displaces the imaging unit in such a manner as to correct a displacement by use of displacements at a plurality of positions within the imaging plane in a case where an object tracking command is not issued, and displaces the imaging unit in such a manner as to correct a displacement by use of a displacement at a specific position within the imaging plane in a case where the object tracking command is issued.

40. An electronic endoscope apparatus according to claim 27, wherein said displacement means further includes imaging unit-positioning means for positioning the imaging unit with reference to the object by performing negative feedback control on the basis of an output from the first displacement-correcting means.

41. An electronic endoscope apparatus according to claim 27, wherein said displacement-calculating means detects how an image of the object is displaced from the imaging unit at a plurality of positions within the imaging plane, said displacement-calculating means including:
   magnification-changing means for changing a magnification of an object image signal supplied from the imaging unit; and
   display signal-generating means for generating a display signal on the basis of the object image signal whose magnification is changed by the magnification-changing means.

42. An electronic endoscope apparatus according to claim 41, wherein said displacement means further includes means for determining a displacement type on the basis of said plurality of displacements which the displacement-calculating means detects at said plurality of positions of the imaging plane with respect to the image of the object, said imaging unit being displaced in accordance with the displacement type determined by the displacement type-determining means.

43. An electronic endoscope apparatus according to claim 41, wherein said displacement means further includes magnification-calculating means for calculating a magnification of an object image signal in accordance with said plurality of displacements which the displacement-calculating means detects at said plurality of positions of the imaging plane with respect to the image of the object, said magnification-calculating means changing the magnification of the image of the object in accordance with the magnification-calculating means.

44. An electronic endoscope apparatus according to claim 41, wherein:
   said displacement means further includes displacement-detecting means for obtaining a parallel-movement component and a magnification component of an object image signal in accordance with said plurality of displacements which the displacement-calculating means detects at said plurality of positions of the imaging plane with respect to the image of the object;
   said imaging unit is displaced such that the parallel-movement component of the object image signal is moved in accordance with the parallel-movement component supplied from the displacement-detecting means; and
   said magnification-changing means changes the magnification of the object image signal in accordance with the magnification component supplied from the displacement-detecting means.

45. An electronic endoscope apparatus according to claim 27, wherein said displacement means further includes switching means for selecting one of the first and second displacement-correcting means.

* * * * *